(12) United States Patent
Mio et al.

(10) Patent No.: US 9,425,484 B2
(45) Date of Patent: Aug. 23, 2016

(54) NON-AQUEOUS ELECTROLYTE SOLUTION CONTAINING PHOSPHONOSULFONIC ACID COMPOUND, AND LITHIUM SECONDARY BATTERY

(71) Applicant: Mitsui Chemicals, Inc., Tokyo (JP)

(72) Inventors: Shigeru Mio, Chiba (JP); Mitsuo Nakamura, Chosei-gun (JP); Hidenobu Nogi, Chiba (JP); Satoko Fujiyama, Kisarazu (JP); Hidetoshi Tsunoda, Awa-gun (JP)

(73) Assignee: MITSUI CHEMICALS, INC., Tokyo (JP)

( * ) Notice: Subject to any disclaimer, the term of this patent is extended or adjusted under 35 U.S.C. 154(b) by 148 days.

(21) Appl. No.: 14/350,415

(22) PCT Filed: Oct. 19, 2012

(86) PCT No.: PCT/JP2012/077162
§ 371 (c)(1),
(2) Date: Apr. 8, 2014

(87) PCT Pub. No.: WO2013/058387
PCT Pub. Date: Apr. 25, 2013

(65) Prior Publication Data
US 2014/0272556 A1  Sep. 18, 2014

(30) Foreign Application Priority Data

Oct. 21, 2011 (JP) ................. 2011-231618

(51) Int. Cl.
*H01M 10/0567* (2010.01)
*C07F 9/6574* (2006.01)
(Continued)

(52) U.S. Cl.
CPC ......... *H01M 10/0567* (2013.01); *C07F 9/3808* (2013.01); *C07F 9/4006* (2013.01);
(Continued)

(58) Field of Classification Search
CPC .... C07F 9/3808; C07F 9/4006; C07F 9/4075; C07F 9/409; C07F 9/65742; C07F 9/65748; H01M 10/052; H01M 10/0567; Y02E 60/122; Y02T 10/7011
See application file for complete search history.

(56) References Cited

U.S. PATENT DOCUMENTS

2008/0138714 A1   6/2008 Ihara et al.
2008/0138715 A1*  6/2008 Ihara ................... H01M 10/052
                                                           429/338

FOREIGN PATENT DOCUMENTS

JP   2-184693 A   7/1990
JP   9-27328  A   1/1997
(Continued)

OTHER PUBLICATIONS

Krzysztof Hoffman. Novel Sulfur-Containing Electrophiles in Asymmetric Organocatalysis. Dissertation Oct. 13, 2008.*
(Continued)

*Primary Examiner* — Carlos Barcena
(74) *Attorney, Agent, or Firm* — Buchanan, Ingersoll & Rooney PC

(57) ABSTRACT

The invention provides a non-aqueous electrolyte solution containing a phosphonosulfonic acid compound represented by formula (I):
wherein, in formula (I), $R^1$, $R^2$ and $R^3$ each independently represent a hydrogen atom, an alkyl group having 1 to 6 carbon atoms, a haloalkyl group having 1 to 6 carbon atoms, a phenyl group, a benzyl group, or a group represented by formula (II); $R^4$ and $R^5$ each independently represent a hydrogen atom, a halogen atom, or an alkyl group having 1 to 6 carbon atoms; and n represents an integer from 1 to 6; and
wherein, in formula (II), $R^6$, $R^7$ and $R^8$ each independently represent an alkyl group having 1 to 6 carbon atoms, a phenyl group, or a benzyl group; m represents an integer from 0 to 2; and * represents a position of bonding with the oxygen atom in formula (I).

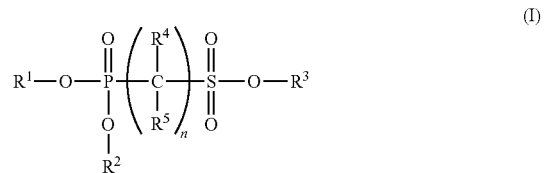

(I)

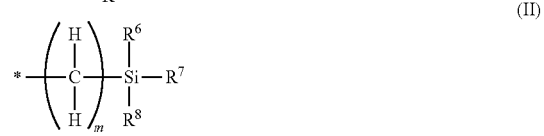

(II)

14 Claims, 1 Drawing Sheet

(51) Int. Cl.
*C07F 9/38* (2006.01)
*C07F 9/40* (2006.01)
*H01M 10/052* (2010.01)

(52) U.S. Cl.
CPC .............. *C07F 9/409* (2013.01); *C07F 9/4075* (2013.01); *C07F 9/65742* (2013.01); *C07F 9/65748* (2013.01); *H01M 10/052* (2013.01); *H01M 2300/0025* (2013.01); *Y02E 60/122* (2013.01); *Y02T 10/7011* (2013.01)

(56) References Cited

FOREIGN PATENT DOCUMENTS

| | | |
|---|---|---|
| JP | 10-189039 A | 7/1998 |
| JP | 3658506 B2 | 6/2005 |
| JP | 2008-262908 A | 10/2008 |
| JP | 2009-70615 A | 4/2009 |
| JP | 4538886 B2 | 9/2010 |
| WO | WO 2011/096450 A1 | 8/2011 |

OTHER PUBLICATIONS

Prishchenko, Andrey A.; Livantsov, Mikhail V.;Novikova, Olga P.; Livantsova, Ludmila I.; Petrosyan, Valery S. Synthesis of new organophosphorus-substituted derivatives of ethanesulfonic acid, Heteroatom Chemistry 2008, 19(5), 470-473.*

Extended Search Report issued by the European Patent Office in corresponding European Patent Application No. 12842359.7 on Jun. 3, 2015 (6 pages).

International Search Report (PCT/ISA/210) mailed on Dec. 4, 2012, by the Japanese Patent Office as the International Searching Authority for International Application No. PCT/JP2012/077162.

Written Opinion (PCT/ISA/237) mailed on Dec. 4, 2012, by the Japanese Patent Office as the International Searching Authority for International Application No. PCT/JP2012/077162.

A. Prishchenko et al., Synthesis of 2-P-Substituted Derivatives of Ethanesulfonic Acid, Russian Journal of General Chemistry, vol. 74, No. 11, 2004, pp. 1820-1821.

Office Action issued by the Chinese Patent Office in corresponding Chinese Patent Application No. 201280049604.4 on Aug. 31, 2015 (13 pages including partial translation).

* cited by examiner

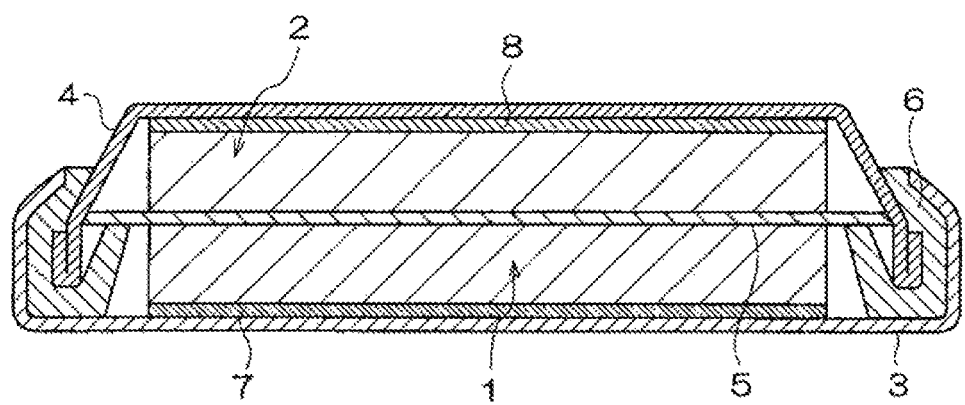

NON-AQUEOUS ELECTROLYTE SOLUTION CONTAINING PHOSPHONOSULFONIC ACID COMPOUND, AND LITHIUM SECONDARY BATTERY

TECHNICAL FIELD

The present invention relates to a non-aqueous electrolyte solution containing a phosphonosulfonic acid compound, a lithium secondary battery including the non-aqueous electrolyte solution, an additive for a lithium secondary battery containing a phosphonosulfonic acid compound, and a phosphonosulfonic acid compound.

BACKGROUND ART

In recent years, lithium secondary batteries are widely used as power sources for electronic devices such as mobile telephones and notebook computers, or for electric cars or electric power storage. Particularly recently, there is a rapidly increasing demand for a high capacity and high power battery with a high energy density, which can be mounted in hybrid cars or electric cars.

Lithium secondary batteries are primarily composed of a positive electrode and a negative electrode, which contain materials capable of absorption and desorption of lithium, and a non-aqueous electrolyte solution containing a lithium salt and a non-aqueous solvent.

Examples of positive electrode active materials used in a positive electrode include lithium metal oxides such as $LiCoO_2$, $LiMnO_2$, $LiNiO_2$, and $LiFePO_4$.

Furthermore, as the non-aqueous electrolyte solution, solutions prepared by mixing a mixed solvent (non-aqueous solvent) of carbonates such as ethylene carbonate, propylene carbonate, ethylene carbonate or methyl carbonate, with a Li electrolyte such as $LiPF_6$, $LiBF_4$, $LiN(SO_2CF_3)_2$ or $LiN(SO_2CF_2CF_3)_2$, are used.

On the other hand, as the active material for a negative electrode that is used in negative electrodes, metal lithium, metal compounds (elemental metals, oxides, alloys with lithium, and the like) capable of absorption and desorption of lithium, and carbon materials are known. Particularly, lithium secondary batteries employing cokes, artificial graphite or natural graphite, which are all capable of absorption and desorption of lithium, have been put to practical use.

Among the battery performances, particularly in relation to lithium secondary batteries for automotive applications, an increase in output power and an increase in service life are required. It has been a considerable challenge to achieve a balance between a reduction of the resistance of a battery under various conditions and an enhancement of the service life performance of a battery.

One of the factors known to cause an increase in the resistance of a battery is a passivation film based on a solvent decomposition product or an inorganic salt, which is formed on the surface of a negative electrode. In general, it is known that since lithium metal is present among the negative electrode active material under the charging conditions, a reductive decomposition reaction of the electrolyte solution occurs at the surface of the negative electrode. In a case in which such reductive decomposition continuously occurs, the resistance of the battery increases, the charge-discharge efficiency decreases, and the energy density of the battery decreases. Furthermore, on the other hand, it is also known in regard to the positive electrode that a deterioration reaction occurs over time, the resistance continually increases, and a decrease in the battery performance is caused. In order to overcome these problems, attempts have been made to add various compounds to electrolyte solution.

As an attempt, for example, a technique of adding a specific silyl phosphate compound to a non-aqueous electrolyte solution, thereby improving the storage performance of the battery has been proposed (see, for example, Japanese Patent No. 4538886).

Furthermore, there have been examined: a technique of adding a specific sulfonate compound to improve the impregnation into the separator of the battery, thereby improving the battery capacity and battery voltage (see, for example, Japanese Patent Application Laid-Open (JP-A) No. H9-27328); a technique of adding 1,3-propanesultone, which is a cyclic sulfonate derivative, as a specific sulfonate, thereby improving the cycle characteristics (see, for example, Japanese Patent No. 3658506); and a technique of adding a specific phosphonocarboxylic acid, thereby improving flame-retardancy of the electrolyte solution, and charge and discharge characteristics of the battery (see, for example, JP-A No. H10-189039);

Furthermore, there have been examined a technique of adding a specific phosphonocarboxylic acid, thereby improving the storage characteristics of the electrolyte solution, specifically the amount of gas emission and residual capacity after continuous charge, and the residual capacity after high temperature storage (see, for example, JP-A Nos. 2008-262908 and 2009-70615).

SUMMARY OF INVENTION

Technical Problem

However, under circumstances where an increase in output power and an increase in service life are required, a balance between an improvement in the low temperature discharge characteristics of the battery and an improvement in the storage characteristics of the battery cannot be sufficiently achieved by the prior art alone.

The invention was achieved in order to cope with the problem described above, and an object of the invention is to provide a non-aqueous electrolyte solution which can achieve a balance between an improvement in the low temperature discharge characteristics of a battery and an improvement in the storage characteristics of the battery, and a lithium secondary battery using the non-aqueous electrolyte solution.

Another object of the invention is to provide an additive for a lithium secondary battery useful for the non-aqueous electrolyte solution, and a phosphonosulfonic acid compound useful as the additive for a lithium secondary battery.

Solution to Problem

The inventors diligently studied the problem described above, and have found that the inclusion of a specific phosphonosulfonic acid compound in the non-aqueous electrolyte solution of a lithium secondary battery can achieve a balance between an improvement in the low temperature discharge characteristics of a battery and an improvement in the storage characteristics of the battery, and have thus accomplished the invention.

That is, specific means for solving the problem described above are as follows.

<1> A non-aqueous electrolyte solution comprising a phosphonosulfonic acid compound represented by the following formula (I):

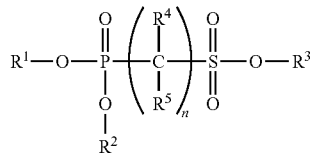

(I)

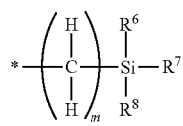

(II)

wherein, in formula (I), $R^1$, $R^2$ and $R^3$ each independently represent a hydrogen atom, an alkyl group having 1 to 6 carbon atoms, a haloalkyl group having 1 to 6 carbon atoms, a phenyl group, a benzyl group, or a group represented by the above formula (II); $R^4$ and $R^5$ each independently represent a hydrogen atom, a halogen atom, or an alkyl group having 1 to 6 carbon atoms; and n represents an integer from 1 to 6; and wherein, in formula (II), $R^6$, $R^7$ and $R^8$ each independently represent an alkyl group having 1 to 6 carbon atoms, a phenyl group, or a benzyl group; m represents an integer from 0 to 2; and * represents a position of bonding with the oxygen atom in formula (I).

<2> The non-aqueous electrolyte solution according to <1>, wherein the phosphonosulfonic acid compound represented by formula (I) is a phosphonosulfonic acid compound represented by the following formula (III):

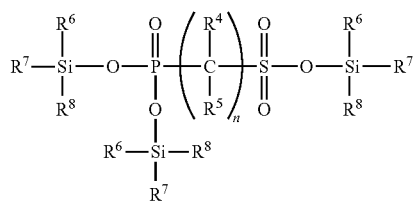

(III)

wherein, in formula (III), $R^4$ and $R^5$ each independently represent a hydrogen atom, a halogen atom, or an alkyl group having 1 to 6 carbon atoms; $R^6$, $R^7$ and $R^8$ each independently represent an alkyl group having 1 to 6 carbon atoms, a phenyl group, or a benzyl group; and n represents an integer from 1 to 6.

<3> The non-aqueous electrolyte solution according to <1> or <2>, further comprising a compound represented by the following formula (IV):

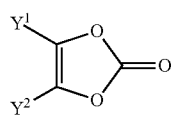

(IV)

wherein, in formula (IV), $Y^1$ and $Y^2$ each independently represent a hydrogen atom, a methyl group, an ethyl group, or a propyl group.

<4> The non-aqueous electrolyte solution according to any one of <1> to <3>, further comprising a compound represented by the following formula (V):

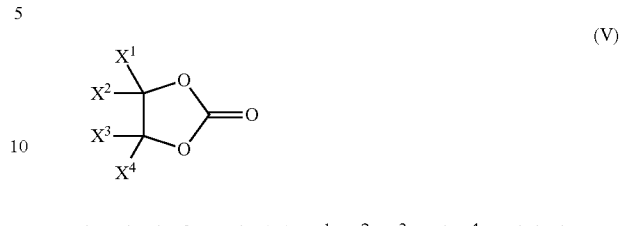

(V)

wherein, in formula (V), $X^1$, $X^2$, $X^3$ and $X^4$ each independently represent a vinyl group; an alkyl group having 1 to 3 carbon atoms, which may be substituted with a fluorine atom; a hydrogen atom; a fluorine atom; or a chlorine atom; provided that $X^1$, $X^2$, $X^3$ and $X^4$ are not all hydrogen atoms at the same time.

<5> The non-aqueous electrolyte solution according to any one of <1> to <4>, further comprising a compound represented by the following formula (VI):

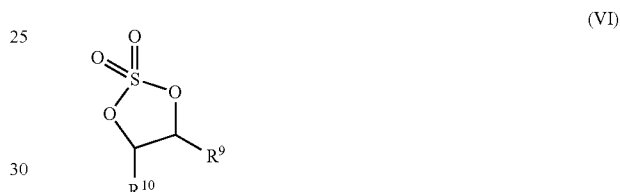

(VI)

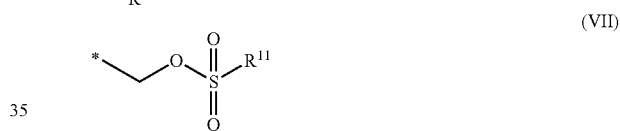

(VII)

(VIII)

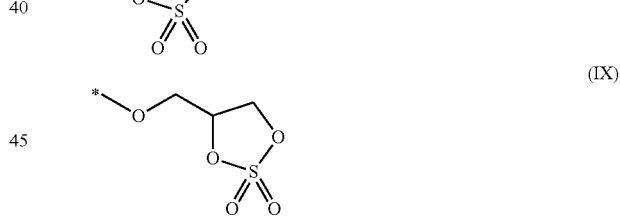

(IX)

wherein, in formula (VI), $R^9$ and $R^{10}$ each independently represent a hydrogen atom, an alkyl group having 1 to 6 carbon atoms, a group represented by the above formula (VII), or a group represented by the above formula (VIII);

wherein, in formula (VII), $R^{11}$ represents a halogen atom, an alkyl group having 1 to 6 carbon atoms, a haloalkyl group having 1 to 6 carbon atoms, an alkoxy group having 1 to 6 carbon atoms, or a group represented by the above formula (IX); and wherein, in formulae (VII), (VIII), and (IX), * represents a position of bonding.

<6> The non-aqueous electrolyte solution according to any one of <1> to <5>, further comprising at least one compound selected from the group consisting of lithium difluorophosphate ($LiOP(O)F_2$), a compound represented by the following formula (X), a compound represented by the following formula (XI), and a compound represented by the following formula (XII):

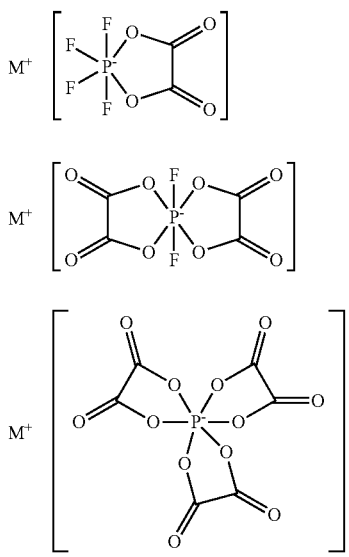

(X), (XI), (XII)

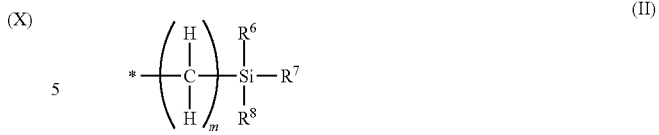

(II)

wherein, in formulae (X), (XI), and (XII), M represents an alkali metal.

<7> The non-aqueous electrolyte solution according to any one of <1> to <6>, wherein the content of the phosphonosulfonic acid compound represented by formula (I) is from 0.001% by mass to 10% by mass relative to the total mass of the non-aqueous electrolyte solution.

<8> The non-aqueous electrolyte solution according to <3>, wherein the content of the compound represented by formula (IV) is from 0.001% by mass to 10% by mass relative to the total mass of the non-aqueous electrolyte solution.

<9> The non-aqueous electrolyte solution according to <4>, wherein the content of the compound represented by formula (V) is from 0.001% by mass to 10% by mass relative to the total mass of the non-aqueous electrolyte solution.

<10> The non-aqueous electrolyte solution according to <5>, wherein the content of the compound represented by formula (VI) is from 0.001% by mass to 10% by mass relative to the total mass of the non-aqueous electrolyte solution.

<11> The non-aqueous electrolyte solution according to <6>, wherein a total content of lithium difluorophosphate (LiOP(O)F$_2$), the compound represented by formula (X), the compound represented by formula (XI), and the compound represented by formula (XII) is from 0.001% by mass to 10% by mass relative to the total mass of the non-aqueous electrolyte solution.

<12> An additive for a lithium secondary battery, comprising a phosphonosulfonic acid compound represented by the following formula (I):

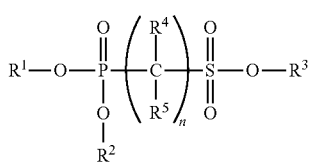

(I)

wherein, in formula (I), $R^1$, $R^2$ and $R^3$ each independently represent a hydrogen atom, an alkyl group having 1 to 6 carbon atoms, a haloalkyl group having 1 to 6 carbon atoms, a phenyl group, a benzyl group, or a group represented by the above formula (II); $R^4$ and $R^5$ each independently represent a hydrogen atom, a halogen atom, or an alkyl group having 1 to 6 carbon atoms; and n represents an integer from 1 to 6; and wherein, in formula (II), $R^6$, $R^7$ and $R^8$ each independently represent an alkyl group having 1 to 6 carbon atoms, a phenyl group, or a benzyl group; m represents an integer from 0 to 2, and * represents a position of bonding with the oxygen atom in formula (I).

<13> A phosphonosulfonic acid compound represented the following formula (XIII):

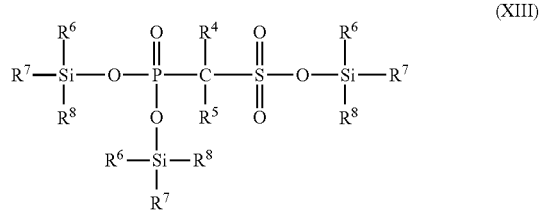

(XIII)

wherein, in formula (XIII), $R^4$ and $R^5$ each independently represent a hydrogen atom, a halogen atom, or an alkyl group having 1 to 6 carbon atoms; and $R^6$, $R^7$ and $R^8$ each independently represent an alkyl group having 1 to 6 carbon atoms, a phenyl group, or a benzyl group.

<14> A lithium secondary battery, comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the non-aqueous electrolyte solution according to any one of <1> to <11>.

<15> A lithium secondary battery, obtained by charging and discharging a lithium secondary battery comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the non-aqueous electrolyte solution according to any one of <1> to <11>.

Advantageous Effects of the Invention

According to the invention, a non-aqueous electrolyte solution which can achieve a balance between an improvement in the low temperature discharge characteristics of a battery and an improvement in the storage characteristics of the battery, and a lithium secondary battery using the non-aqueous electrolyte solution can be provided.

Furthermore, according to the invention, an additive for a lithium secondary battery useful for the non-aqueous electrolyte solution, and a phosphonosulfonic acid compound useful as the additive for a lithium secondary battery can be provided.

BRIEF DESCRIPTION OF DRAWINGS

FIG. 1 is a schematic cross sectional view of a coin battery showing an example of the lithium secondary battery of the invention.

DESCRIPTION OF EMBODIMENTS

A non-aqueous electrolyte solution including the phosphonosulfonic acid compound of the invention, a lithium secondary battery including the non-aqueous electrolyte solution, and an additive for a lithium secondary battery useful for the non-aqueous electrolyte solution are specifically described below.

<Non-Aqueous Electrolyte Solution>

The non-aqueous electrolyte solution of the invention contains a phosphonosulfonic acid compound represented by the following formula (I). The non-aqueous electrolyte solution of the invention may optionally contain other components.

Due to the composition of the non-aqueous electrolyte solution of the invention, when used in a battery, the non-aqueous electrolyte solution can achieve a balance between an improvement in the low temperature discharge characteristics of the battery and an improvement in the storage characteristics of the battery.

Accordingly, when the non-aqueous electrolyte solution of the invention is used in a lithium secondary battery, the lithium secondary battery achieves excellent low temperature discharge characteristics and excellent storage characteristics.

[Phosphonosulfonic Acid Compound]

The phosphonosulfonic acid compound in the invention is a phosphonosulfonic acid compound represented by the following formula (I) (hereinafter may be simply referred to as "the compound represented by formula (I)").

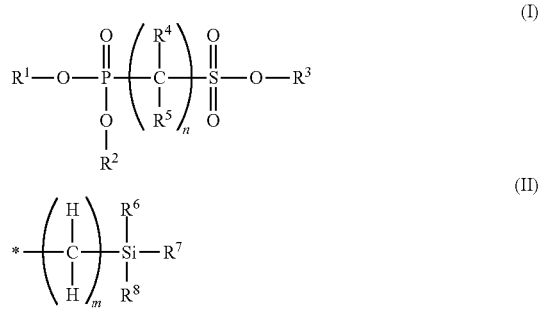

In formula (I), $R^1$, $R^2$ and $R^3$ each independently represent a hydrogen atom, an alkyl group having 1 to 6 carbon atoms, a haloalkyl group having 1 to 6 carbon atoms, a phenyl group, a benzyl group, or a group represented by the above formula (II), $R^4$ and $R^5$ each independently represent a hydrogen atom, a halogen atom, or an alkyl group having 1 to 6 carbon atoms, and n represents an integer from 1 to 6.

When n represents an integer from 2 to 6, the plural $R^4$s and $R^5$s may be identical or different.

In formula (II), $R^6$, $R^7$ and $R^8$ represent an alkyl group having 1 to 6 carbon atoms, a phenyl group, or a benzyl group, and m represents an integer from 0 to 2. * represents a position of bonding with the oxygen atom in formula (I).

When two or more groups represented by formula (II) are contained in the compound represented by formula (I), the two or more groups represented by formula (II) may be identical or different.

In the present description, unless otherwise noted, the "alkyl group" includes a linear alkyl group, a branched alkyl group, and a cyclic alkyl group.

In addition, in the present description, the "haloalkyl group" means an alkyl halide group.

In formula (I), the "alkyl group having 1 to 6 carbon atoms" is preferably a linear alkyl group or a branched alkyl group having 1 to 6 carbon atoms, and specific examples thereof include a methyl group, an ethyl group, an n-propyl group, an isopropyl group, an n-butyl group, an isobutyl group, a sec-butyl group, a tert-butyl group, a pentyl group, a 2-methylbutyl group, a 1-methylpentyl group, a neopentyl group, a 1-ethylpropyl group, a hexyl group, and a 3,3-dimethylbutyl group. The alkyl group is preferably a linear alkyl group or a branched alkyl group having 1 to 4 carbon atoms.

In formula (I), the "haloalkyl group having 1 to 6 carbon atoms" represents the haloalkyl group in which at least one hydrogen atom in the linear alkyl group or the branched alkyl group having 1 to 6 carbon atoms is substituted with halogen atom(s), and specific examples thereof include a fluoromethyl group, a difluoromethyl group, a trifluoromethyl group, a 2,2,2-trifluoroethyl group, a perfluoroethyl group, a perfluoropropyl group, a perfluorobutyl group, a perfluoropentyl group, a perfluorohexyl group, a perfluoroisopropyl group, a perfluoroisobutyl group, a chloromethyl group, a chloroethyl group, a chloropropyl group, a bromomethyl group, a bromoethyl group, a bromopropyl group, a methyl iodide group, an ethyl iodide group, and a propyl iodide group.

The haloalkyl group having 1 to 6 carbon atoms is more preferably a haloalkyl group having 1 to 3 carbon atoms.

In formula (I), specific examples of the "halogen atom" include a fluorine atom, a chlorine atom, a bromine atom, and an iodine atom.

The halogen atom is preferably a fluorine atom.

In formula (I), the phenyl group may be unsubstituted or substituted.

Examples of the substituent which may be introduced into the phenyl group include a halogen atom, an alkyl group having 1 to 6 carbon atoms, a haloalkyl group having 1 to 6 carbon atoms, and an alkoxy group having 1 to 6 carbon atoms.

In the substituents which may be introduced into the phenyl group, specific examples of the "halogen atom" include a fluorine atom, a chlorine atom, a bromine atom, and an iodine atom.

The halogen atom is preferably a fluorine atom.

In the substituents which may be introduced into the phenyl group, the "alkyl group having 1 to 6 carbon atoms" is the same with the above-described "alkyl group having 1 to 6 carbon atoms", and their preferred embodiments are the same.

In the substituents which may be introduced into the phenyl group, the "haloalkyl group having 1 to 6 carbon atoms" is the same with the above-described "haloalkyl group having 1 to 6 carbon atoms", and their preferred embodiments are the same.

In the substituents which may be introduced into the phenyl group, the "alkoxy group having 1 to 6 carbon atoms" is a linear alkoxy group or a branched alkoxy group having 1 to 6 carbon atoms, and specific examples thereof include a methoxy group, an ethoxy group, an n-propoxy group, an isopropoxy group, an n-butoxy group, an isobutoxy group, a sec-butoxy group, a tert-butoxy group, a pentyloxy group, a 2-methylbutoxy group, a 1-methylpentyloxy group, a neopentyloxy group, a 1-ethylpropoxy group, a hexyloxy group, and a 3,3-dimethylbutoxy group.

The alkoxy group having 1 to 6 carbon atoms is more preferably an alkoxy group having 1 to 3 carbon atoms.

In formula (I), the benzyl group may be unsubstituted or substituted.

Examples of the substituent which may be introduced into the benzyl group include a halogen atom, an alkyl group having 1 to 6 carbon atoms, a haloalkyl group having 1 to 6 carbon atoms, and an alkoxy group having 1 to 6 carbon atoms.

In the substituent which may be introduced into the benzyl group, the "halogen atom", "alkyl group having 1 to 6 carbon atoms", "haloalkyl group having 1 to 6 carbon atoms", and "alkoxy group having 1 to 6 carbon atoms" are the same with the "halogen atom", "alkyl group having 1 to 6 carbon atoms", "haloalkyl group having 1 to 6 carbon atoms", and "alkoxy group having 1 to 6 carbon atoms" included in the substituent which may be introduced into the phenyl group, respectively.

The "alkyl group having 1 to 6 carbon atoms", "phenyl group", and "benzyl group" in formula (II) are the same as the above-described "alkyl group having 1 to 6 carbon atoms", "phenyl group", and "benzyl group", respectively.

In formula (I), n represents an integer from 1 to 6 as described above, and is preferably an integer from 1 to 2.

In addition, the phosphonosulfonic acid compound represented by formula (I) is particularly preferably a phosphonosulfonic acid compound represented by the following formula (III).

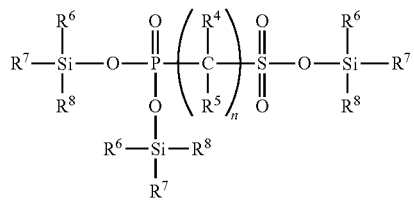

(III)

In formula (III), $R^4$ and $R^5$ each independently represent a hydrogen atom, a halogen atom, or an alkyl group having 1 to 6 carbon atoms, $R^6$, $R^7$ and $R^8$ each independently represent an alkyl group having 1 to 6 carbon atoms, a phenyl group, or a benzyl group, and n represents an integer from 1 to 6.

The "halogen atom", "alkyl group having 1 to 6 carbon atoms", "phenyl group", and "benzyl group" in formula (III) are the same as the "halogen atom", "alkyl group having 1 to 6 carbon atoms", "phenyl group", and "benzyl group" in formula (I), respectively.

In addition, in formula (III), n represents an integer from 1 to 6, and is preferably an integer from 1 to 2.

Particularly preferred examples of the phosphonosulfonic acid compound represented by formula (I) include trimethylsilyl bis(trimethylsilyl) phosphonomethanesulfonate, trimethylsilylmethyl bis(trimethylsilylmethyl) phosphonomethanesulfonate, phosphonomethanesulfonic acid, methyl diethyl phosphonomethanesulfonate, phenyl 2-(diethoxyphosphoryl) ethanesulfonate, and phenyl 2-(hydroxy (trimethylsilyloxy)phosphoryl) ethanesulfonate.

The phosphonosulfonic acid compound represented by formula (I) is, as will be described later, useful as an additive for a lithium secondary battery (preferably, an additive for a non-aqueous electrolyte solution of a lithium secondary battery).

Specific examples of the phosphonosulfonic acid compound represented by formula (I) in the invention [exemplary compounds 1 to 118] are shown below in which the substituents in formula (I) are defined, but the invention will not be limited to these compounds.

In the structure of the following exemplary compounds, "Me" represents a methyl group, "Et" represents an ethyl group, "Pr" represents an n-propyl group, "iPr" represents an isopropyl group, "Bu" represents an n-butyl group, "t-Bu" represents a tertiary butyl group, "Pent" represents a pentyl group, "Hex" represents a hexyl group, "Ph" represents a phenyl group, and "Bn" represents a benzyl group, respectively.

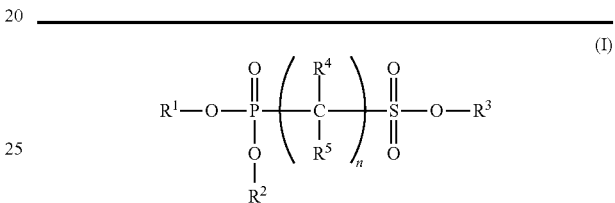

(I)

| Exemplary compound | n | $R^1$ | $R^2$ | $R^3$ | $R^4$ | $R^5$ |
|---|---|---|---|---|---|---|
| 1 | 1 | H | H | H | H | H |
| 2 | 1 | Me | Me | Me | H | H |
| 3 | 1 | Me | Me | Et | H | H |
| 4 | 1 | Me | Me | Pr | H | H |
| 5 | 1 | Me | Me | Bu | H | H |
| 6 | 1 | Me | Me | Pent | H | H |
| 7 | 1 | Me | Me | Hex | H | H |
| 8 | 1 | Me | Me | Ph | H | H |
| 9 | 1 | Me | Me | Bn | H | H |
| 10 | 1 | Et | Et | Me | H | H |
| 11 | 1 | Et | Et | Et | H | H |
| 12 | 1 | Et | Et | Ph | H | H |
| 13 | 1 | Pr | Pr | Me | H | H |
| 14 | 1 | Bu | Bu | Me | H | H |
| 15 | 1 | Pent | Pent | Me | H | H |
| 16 | 1 | Hex | Hex | Me | H | H |
| 17 | 1 | H | H | H | F | H |
| 18 | 1 | H | H | H | F | F |
| 19 | 1 | H | H | H | Me | H |
| 20 | 1 | H | H | H | Me | Me |
| 21 | 1 | H | H | H | Et | H |
| 22 | 1 | H | H | H | Et | Et |
| 23 | 1 | SiMe$_3$ | SiMe$_3$ | SiMe$_3$ | H | H |
| 24 | 1 | SiMe$_3$ | SiMe$_3$ | Me | H | H |
| 25 | 1 | SiMe$_3$ | SiMe$_3$ | Et | H | H |
| 26 | 1 | SiMe$_3$ | SiMe$_3$ | Pr | H | H |
| 27 | 1 | SiMe$_3$ | SiMe$_3$ | Bu | H | H |
| 28 | 1 | SiMe$_3$ | SiMe$_3$ | Pent | H | H |
| 29 | 1 | SiMe$_3$ | SiMe$_3$ | Hex | H | H |
| 30 | 1 | SiMe$_3$ | SiMe$_3$ | SiMe$_3$ | H | H |
| 31 | 1 | SiMe$_2$Ph | SiMe$_2$Ph | SiMe$_2$Ph | H | H |
| 32 | 2 | H | H | H | H | H |
| 33 | 2 | Me | Me | Me | H | H |
| 34 | 2 | Me | Me | Et | H | H |
| 35 | 2 | Me | Me | Pr | H | H |
| 36 | 2 | Me | Me | Bu | H | H |
| 37 | 2 | Me | Me | Pent | H | H |
| 38 | 2 | Me | Me | Hex | H | H |
| 39 | 2 | Me | Me | Ph | H | H |
| 40 | 2 | Me | Me | Bn | H | H |
| 41 | 2 | Et | Et | Me | H | H |
| 42 | 2 | Et | Et | Et | H | H |
| 43 | 2 | Et | Et | Ph | H | H |
| 44 | 2 | Pr | Pr | Me | H | H |
| 45 | 2 | Bu | Bu | Me | H | H |

-continued

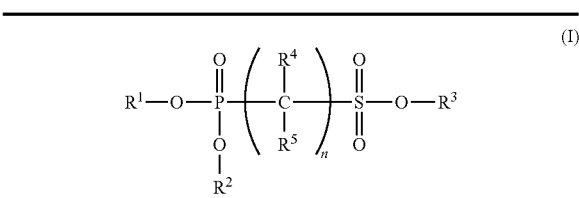

(I)

| Exemplary compound | n | R¹ | R² | R³ | R⁴ | R⁵ |
|---|---|---|---|---|---|---|
| 46 | 2 | Pent | Pent | Me | H | H |
| 47 | 2 | Hex | Hex | Me | H | H |
| 48 | 2 | H | H | H | F | H |
| 49 | 2 | H | H | H | F | F |
| 50 | 2 | H | H | H | Me | H |
| 51 | 2 | H | H | H | Me | Me |
| 52 | 2 | H | H | H | Et | H |
| 53 | 2 | H | H | H | Et | Et |
| 54 | 2 | SiMe₃ | SiMe₃ | SiMe₃ | H | H |
| 55 | 2 | SiMe₃ | SiMe₃ | Me | H | H |
| 56 | 2 | SiMe₃ | SiMe₃ | Et | H | H |
| 57 | 2 | SiMe₃ | SiMe₃ | Pr | H | H |
| 58 | 2 | SiMe₃ | SiMe₃ | Bu | H | H |
| 59 | 2 | SiMe₃ | SiMe₃ | Pent | H | H |
| 60 | 2 | SiMe₃ | SiMe₃ | Hex | H | H |
| 61 | 2 | SiEt₃ | SiEt₃ | SiEt₃ | H | H |
| 62 | 2 | SiMe₂Ph | SiMe₂Ph | SiMe₂Ph | H | H |
| 63 | 3 | H | H | H | H | H |
| 64 | 3 | SiMe₃ | SiMe₃ | SiMe₃ | H | H |
| 65 | 4 | H | H | H | H | H |
| 66 | 4 | SiMe₃ | SiMe₃ | SiMe₃ | H | H |
| 67 | 5 | H | H | H | H | H |
| 68 | 5 | SiMe₃ | SiMe₃ | SiMe₃ | H | H |
| 69 | 6 | H | H | H | H | H |
| 70 | 6 | SiMe₃ | SiMe₃ | SiMe₃ | H | H |
| 71 | 1 | CH₂SiMe₃ | CH₂SiMe₃ | CH₂SiMe₃ | H | H |
| 72 | 1 | SiMe₃ | SiMe₃ | tBu | H | H |
| 73 | 1 | SiMe₃ | SiMe₃ | Ph | H | H |
| 74 | 1 | CH₂CH₂SiMe₃ | CH₂CH₂SiMe₃ | Me | H | H |
| 75 | 1 | CH₂CH₂SiMe₃ | CH₂CH₂SiMe₃ | Et | H | H |
| 76 | 1 | CH₂CH₂SiMe₃ | CH₂CH₂SiMe₃ | tBu | H | H |
| 77 | 1 | CH₂CH₂SiMe₃ | CH₂CH₂SiMe₃ | Ph | H | H |
| 78 | 1 | SiMe₂Bn | SiMe₂Bn | SiMe₂Bn | H | H |
| 79 | 1 | SiMe₂(t-Bu) | SiMe₂(t-Bu) | SiMe₂(t-Bu) | H | H |
| 80 | 2 | SiMe₃ | SiMe₃ | Ph | H | H |
| 81 | 2 | SiMe₃ | H | Ph | H | H |
| 82 | 2 | H | H | Ph | H | H |
| 83 | 1 | CH₂CF₃ | CH₂CF₃ | Me | H | H |
| 84 | 1 | CH₂CF₃ | CH₂CF₃ | Et | H | H |
| 85 | 1 | CH₂CF₃ | CH₂CF₃ | Pr | H | H |
| 86 | 1 | CH₂CF₃ | CH₂CF₃ | iPr | H | H |
| 87 | 1 | Me | Me | CH₂CF₃ | H | H |
| 88 | 1 | Et | Et | CH₂CF₃ | H | H |
| 89 | 1 | Pr | Pr | CH₂CF₃ | H | H |
| 90 | 1 | Bn | Bn | Bn | H | H |
| 91 | 1 | Me | Me | SiMe₃ | H | H |
| 92 | 1 | Et | Et | SiMe₃ | H | H |
| 93 | 1 | Pr | Pr | SiMe₃ | H | H |
| 94 | 1 | iPr | iPr | SiMe₃ | H | H |
| 95 | 1 | Me | SiMe₃ | SiMe₃ | H | H |
| 96 | 1 | Et | SiMe₃ | SiMe₃ | H | H |
| 97 | 1 | Pr | SiMe₃ | SiMe₃ | H | H |
| 98 | 1 | iPr | SiMe₃ | SiMe₃ | H | H |
| 99 | 1 | Me | Me | H | H | H |
| 100 | 1 | Et | Et | H | H | H |
| 101 | 1 | Pr | Pr | H | H | H |
| 102 | 1 | iPr | iPr | H | H | H |
| 103 | 1 | Me | H | H | H | H |
| 104 | 1 | Et | H | H | H | H |
| 105 | 1 | Pr | H | H | H | H |
| 106 | 1 | iPr | H | H | H | H |
| 107 | 2 | Me | Me | SiMe₃ | H | H |
| 108 | 2 | Et | Et | SiMe₃ | H | H |
| 109 | 2 | Pr | Pr | SiMe₃ | H | H |
| 110 | 2 | iPr | iPr | SiMe₃ | H | H |
| 111 | 2 | Me | Me | H | H | H |
| 112 | 2 | Et | Et | H | H | H |
| 113 | 2 | Pr | Pr | H | H | H |
| 114 | 2 | iPr | iPr | H | H | H |
| 115 | 2 | Me | H | H | H | H |
| 116 | 2 | Et | H | H | H | H |
| 117 | 2 | Pr | H | H | H | H |
| 118 | 2 | iPr | H | H | H | H |

Among the exemplary compounds, from the viewpoint of improvement the low temperature discharge characteristics of the battery and storage characteristics of the battery, preferred examples include trimethylsilyl bis(trimethylsilyl) phosphonomethanesulfonate, trimethylsilylmethyl bis(trimethylsilylmethyl) phosphonomethanesulfonate, phosphonomethanesulfonic acid, methyl diethyl phosphonomethanesulfonate, phenyl 2-(diethoxyphosphoryl) ethanesulfonate, and phenyl 2-(hydroxy(trimethylsilyloxy)phosphoryl) ethanesulfonate.

Trimethylsilyl bis(trimethylsilyl) phosphonomethanesulfonate, which is an example of the phosphonosulfonic acid compound represented by formula (I) in the invention, may be produced, without limitation, by the process described below.

The phosphonosulfonic acid compound represented by formula (I) in the invention wherein n=1 is produced in accordance with a known method such as:
Tetrahedron, 1987, 43, 5125-5134;
Organic and Biomolecular Chemistry, 2007, 5, 160-168;
Chemische Berichte, 1980, 113, 142-151; or
Tetrahedron Letters, 1987, 28, 1101-1104.

The phosphonosulfonic acid compound represented by formula (III) in the invention wherein n=1 (more specifically, a phosphonosulfonic acid compound represented by the following formula (XIII)) may be produced by, for example (and without limitation), the method described below using a compound represented by the following formula (Ia) as a starting material.

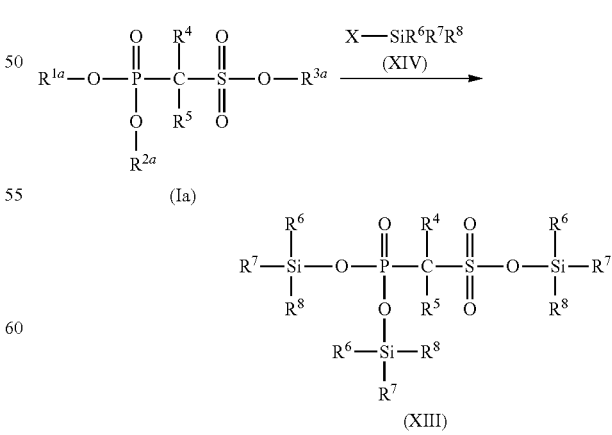

In formula (Ia), $R^{1a}$, $R^{2a}$, and $R^{3a}$ each represents a hydrogen atom or an alkyl group having 1 to 6 carbon atoms. In formulae (Ia), (XIV), and (XIII), $R^4$, $R^5$, $R^6$, $R^7$, and $R^8$ are the same as $R^4$, $R^5$, $R^6$, $R^7$, and $R^8$ in formula (III), respectively.

The production method in accordance with the above scheme is described below in detail.

The phosphonosulfonic acid compound represented by formula (XIII) may be produced by allowing the compound represented by formula (Ia) to react with the silyl compound represented by formula (XIV) without solvent or in the presence of a solvent.

In the silyl compound represented by formula (XIV) used herein, X represents a chlorine atom, a bromine atom, or an iodine atom, and is preferably a bromine atom or an iodine atom.

The solvent used for the reaction is not particularly limited as long as it will not inhibit the reaction and dissolves the starting material to a degree. Examples of the solvent include hydrocarbon halides such as dichloromethane, dichloroethane, and chloroform; aromatic hydrocarbons such as benzene, toluene, xylene, and chlorobenzene; aliphatic hydrocarbons such as hexane, cyclohexane, and heptane; and mixed solvents of any of them. In these compounds, hydrocarbon halides and aromatic hydrocarbons are preferred, and dichloromethane and toluene are more preferred.

The amount of the solvent is normally from 0.1 L to 10 L, and preferably from 0.1 L to 5 L relative to 1 mol of the compound represented by formula (Ia).

The reaction temperature varies depending on, for example, the starting material, reaction reagent, and solvent, but normally may be from 0° C. to the reflux temperature in the reaction system, and is preferably from 10° C. to 40° C.

The reaction period varies depending on, for example, the starting material, reaction reagent, solvent, and reaction temperature, and may be normally from 0.5 hours to 48 hours, and is preferably from 1 hour to 24 hours.

The compound represented by formula (Ia) used in this process may be purchased or prepared by a known method. Specifically, the compound is produced by, for example, the method described in Tetrahedron, 1987, 43, 5125-5134.

The phosphonosulfonic acid compound represented by formula (I) in the invention wherein n=2 is produced in accordance with a known method such as the method described in, for example:

Phosphorus, Sulfur and Silicon and the Related Elements, 1991, 56, 111-115;
Russian Journal of General Chemistry, 2004, 74, 1820-1821; or
Heteroatom Chemistry, 208, 19, 470-473.

The phosphonosulfonic acid compound represented by formula (I) in the invention wherein n=3 to 6 may be produced in accordance with a known method such as the method described in, for example, US206614635 or DE938186.

The phosphonosulfonic acid compound represented by formula (I) is useful as an additive for a lithium secondary battery, particularly as an additive for a non-aqueous electrolyte solution of the lithium secondary battery described below. As a result of the addition of the additive to a non-aqueous electrolyte solution, a lithium secondary battery having excellent low temperature discharge characteristics and excellent storage characteristics is obtained.

A speculated reason why the phosphonosulfonic acid compound represented by formula (I) offers the above-described effects is explained below.

When the phosphonosulfonic acid compound represented by formula (I) is used, during film formation on the negative electrode side by the initial charge, the phosphonosulfonic acid compound represented by formula (I) having this skeleton achieves excellent lithium ion conductivity on the negative electrode side even at low temperatures, and inhibits continuous decomposition of the solvent on the surface of the negative electrode. As a result of this, a battery having excellent initial low temperature discharge characteristics is provided.

In addition, for the storage characteristics of the battery, the phosphonosulfonic acid compound represented by formula (I) has a phosphonic acid structure and a sulfonic acid structure on the same molecule, so that the resistance increase and capacity decrease at the positive electrode side caused by, for example, the structure change of the active material and elution of the transition metal is effectively inhibited, and so that the resistance increase and capacity decrease at the negative electrode side caused by excessive film formation and deposition of transition metals is effectively inhibited. It is speculated that a battery having excellent storage characteristics can be provided by the above mechanism become the main mechanism.

However, the invention will not be limited by the above speculation.

<Novel Phosphonosulfonic Acid Compound>

In the invention, the phosphonosulfonic acid compound represented the following formula (XIII) is a novel compound.

The phosphonosulfonic acid compound represented the following formula (XIII) is the phosphonosulfonic acid compound represented by formula (III) wherein n is 1.

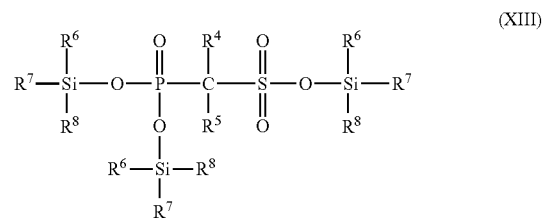

(XIII)

In formula (XIII), $R^4$, $R^5$, $R^6$, $R^7$ and $R^8$ are the same as $R^4$, $R^5$, $R^6$, $R^7$ and $R^8$ in formula (III), respectively.

In formula (XIII), $R^4$ and $R^5$ are each independently preferably a hydrogen atom, a fluorine atom, or an alkyl group having 1 to 3 carbon atoms, and $R^6$, $R^7$, and $R^8$ are each independently preferably a methyl group, an ethyl group, a t-butyl group, a phenyl group, or a benzyl group. The phosphonosulfonic acid compound represented by formula (XIII) is also useful as an additive for a non-aqueous electrolyte solution.

The non-aqueous electrolyte solution of the invention may contain one or more kinds of the phosphonosulfonic acid compound represented by formula (I) (including the phosphonosulfonic acid compound represented by formula (III) or (XIII); hereinafter the same).

In the non-aqueous electrolyte solution of the invention, the content of the phosphonosulfonic acid compound represented by formula (I) is preferably from 0.001% by mass to 10% by mass, and more preferably from 0.05% by mass to 5% by mass relative to the total mass of the non-aqueous electrolyte solution. Within this range, a lithium secondary battery having excellent low temperature discharge characteristics and excellent storage characteristics will be more effectively obtained.

The non-aqueous electrolyte solution of the invention may further contain, as necessary, other components in addition to the phosphonosulfonic acid compound represented by formula (1).

Examples of the other component include, from the viewpoint of more effectively achieving the effect of the invention, at least one selected from the group consisting of the compound represented by formula (IV) described below, the compound represented by formula (V) described below, the compound represented by formula (VI) described below, lithium difluorophosphate (LiOP(O)F$_2$), the compound represented by formula (X) described below, the compound represented by formula (XI) described below, and the compound represented by formula (XII) described below.

Other examples of the other component include electrolytes described below and non-aqueous solvents described below.

The additive for a lithium secondary battery of the invention contains the phosphonosulfonic acid compound represented by formula (I).

As a result of the addition of the additive for a lithium secondary battery of the invention to the non-aqueous electrolyte solution of a lithium secondary battery, as described above, a lithium secondary battery having excellent low temperature discharge characteristics and excellent storage characteristics will be obtained.

The additive for a lithium secondary battery of the invention may further contain, as necessary, other components in addition to the phosphonosulfonic acid compound represented by formula (1).

Examples of the other component include, from the viewpoint of more effectively achieving the effect of the invention, at least one selected from the group consisting of the compound represented by formula (IV) described below, the compound represented by formula (V) described below, the compound represented by formula (VI) described below, lithium difluorophosphate (LiOP(O)F$_2$), the compound represented by formula (X) described below, the compound represented by formula (XI) described below, and the compound represented by formula (XII) described below.

The non-aqueous electrolyte solution of the invention contains, as described above, the phosphonosulfonic acid compound represented by formula (I), and may any known other components.

The other components of the non-aqueous electrolyte solution are described below.

The non-aqueous electrolyte solution commonly contains a non-aqueous solvent and an electrolyte.

[Non-Aqueous Solvent]

Regarding the non-aqueous solvent related to the invention, various known solvents can be appropriately selected, but it is preferable to use a cyclic aprotic solvent and/or a linear aprotic solvent.

When an increase in the flash point of the solvent is intended to enhance the safety of the battery, it is preferable to use a cyclic aprotic solvent as the non-aqueous solvent.

[Cyclic Aprotic Solvent]

Examples of the cyclic aprotic solvent that can be used include a cyclic carbonate, a cyclic carboxylic acid ester, a cyclic sulfone, and a cyclic ether.

The cyclic aprotic solvent may be used alone, or a mixture of plural kinds may also be used.

The mixing proportion of the cyclic aprotic solvent in the non-aqueous solvent is preferably from 10% by mass to 100% by mass, even more preferably from 20% by mass to 90% by mass, and particularly preferably from 30% by mass to 80% by mass. When such a ratio is employed, the conductivity of the electrolyte solution that is related to the charge-discharge characteristics of the battery can be increased.

Specific examples of the cyclic carbonate include ethylene carbonate, propylene carbonate, 1,2-butylene carbonate, 2,3-butylene carbonate, 1,2-pentylene carbonate, and 2,3-pentylene carbonate. Among these, ethylene carbonate and propylene carbonate having high dielectric constants are suitably used. In the case of a battery using graphite as the negative electrode active material, ethylene carbonate is more preferable. Also, two or more kinds of these cyclic carbonates may also be used in mixture.

Specific examples of the cyclic carboxylic acid ester include γ-butyrolactone, δ-valerolactone, and alkyl-substituted forms such as methyl-γ-butyrolactone, ethyl-γ-butyrolactone, and ethyl-δ-valerolactone.

A cyclic carboxylic acid ester has a low vapor pressure, has low viscosity, has a high dielectric constant, and can lower the viscosity of the electrolyte solution without decreasing the flash point of the electrolyte solution and the degree of dissociation of the electrolyte. For this reason, a cyclic carboxylic acid ester has a feature that the conductivity of the electrolyte solution, which is an index associated with the discharge characteristics of a battery, can be increased without increasing the inflammability of the electrolyte solution. Therefore, in the case where an improvement in the flash point of the solvent is intended, it is preferable to use a cyclic carboxylic acid ester as the cyclic aprotic solvent. Among cyclic carboxylic acid esters, γ-butyrolactone is most preferred.

Furthermore, it is preferable to use a cyclic carboxylic acid ester as a mixture with another cyclic aprotic solvent. For example, a mixture of a cyclic carboxylic acid ester and a cyclic carbonate and/or an acyclic carbonate may be used.

Examples of the cyclic sulfone include sulfolane, 2-methylsulfolane, 3-methylsulfolane, dimethylsulfone, diethylsulfone, dipropylsulfone, methylethylsulfone, and methylpropylsulfone.

Examples of the cyclic ether include dioxolane.

[Acyclic Aprotic Solvent]

Examples of the acyclic aprotic solvent of the invention that can be used include an acyclic carbonate, an acyclic carboxylic acid ester, an acyclic ether, and an acyclic phosphoric acid ester.

The mixing proportion of the acyclic aprotic solvent in the non-aqueous solvent is preferably from 10% by mass to 100% by mass, even more preferably from 20% by mass to 90% by mass, and particularly preferably from 30% by mass to 80% by mass.

Specific examples of the acyclic carbonate include dimethyl carbonate, methyl ethyl carbonate, diethyl carbonate, methyl propyl carbonate, methyl isopropyl carbonate, ethyl propyl carbonate, dipropyl carbonate, methyl butyl carbonate, ethyl butyl carbonate, dibutyl carbonate, methyl pentyl carbonate, ethyl pentyl carbonate, dipentyl carbonate, methyl heptyl carbonate, ethyl heptyl carbonate, diheptyl carbonate, methyl hexyl carbonate, ethyl hexyl carbonate, dihexyl carbonate, methyl octyl carbonate, ethyl octyl carbonate, dioctyl carbonate, and methyl trifluoroethyl carbonate. These acyclic carbonates may also be used as mixtures of two or more kinds.

Specific examples of the acyclic carboxylic acid ester include methyl pivalate.

Specific examples of the acyclic ether include dimethoxyethane.

Specific examples of the acyclic phosphoric acid ester include trimethyl phosphate.

[Combination of Solvents]

The non-aqueous solvent used in the non-aqueous electrolyte solution related to the invention may be used singly or as a mixture of plural kinds. Furthermore, only cyclic aprotic solvents may be used singly or as a combination of plural kinds; only acyclic aprotic solvents may be used singly or as a combination of plural kinds; or mixtures of cyclic aprotic solvents and acyclic protic solvents may also be used. Particularly when an enhancement of the rate characteristics and the low temperature characteristics of the battery is intended, it is preferable to use a cyclic aprotic solvent and an acyclic aprotic solvent in combination as the non-aqueous solvent.

Furthermore, in view of the electrochemical stability of the electrolyte solution, it is most preferable to apply a cyclic carbonate as the cyclic aprotic solvent, and to apply an acyclic carbonate as the acyclic aprotic solvent. Furthermore, when a combination of a cyclic carboxylic acid ester and a cyclic carbonate and/or acyclic carbonate is used, the conductivity of the electrolyte solution related to the charge-discharge characteristics of the battery can be increased.

Specific examples of the combination of a cyclic carbonate and an acyclic carbonate include ethylene carbonate with dimethyl carbonate; ethylene carbonate with methyl ethyl carbonate; ethylene carbonate with diethyl carbonate; propylene carbonate with dimethyl carbonate; propylene carbonate with methyl ethyl carbonate; propylene carbonate with diethyl carbonate; ethylene carbonate with propylene carbonate and methyl ethyl carbonate; ethylene carbonate with propylene carbonate and diethyl carbonate; ethylene carbonate with dimethyl carbonate and methyl ethyl carbonate; ethylene carbonate with dimethyl carbonate and diethyl carbonate; ethylene carbonate with methyl ethyl carbonate and diethyl carbonate; ethylene carbonate with dimethyl carbonate, methyl ethyl carbonate and diethyl carbonate; ethylene carbonate with propylene carbonate, dimethyl carbonate and methyl ethyl carbonate; ethylene carbonate with propylene carbonate, dimethyl carbonate and diethyl carbonate; ethylene carbonate with propylene carbonate, methyl ethyl carbonate and diethyl carbonate; and ethylene carbonate with propylene carbonate, dimethyl carbonate, methyl ethyl carbonate and diethyl carbonate.

The mixing proportion of the cyclic carbonate and the acyclic carbonate is such that when expressed as a mass ratio, the ratio of cyclic carbonate: acyclic carbonate is preferably 5:95 to 80:20, more preferably 10:90 to 70:30, and particularly preferably 15:85 to 55:45. When such ratios are employed, an increase in the viscosity of the electrolyte solution is suppressed, and the degree of dissociation of the electrolyte can be increased. Therefore, the conductivity of the electrolyte solution related to the charge-discharge characteristics of a battery can be increased. Furthermore, the solubility of the electrolyte can be further increased. Accordingly, since an electrolyte solution having excellent electrical conductivity at normal temperature or at a low temperature can be obtained, the rate characteristics of a battery at normal temperature to a low temperature can be improved.

Specific examples of the combination of a cyclic carboxylic acid ester with a cyclic carbonate and/or an acyclic carbonate include γ-butyrolactone with ethylene carbonate; γ-butyrolactone with ethylene carbonate and dimethyl carbonate; γ-butyrolactone with ethylene carbonate and methyl ethyl carbonate; γ-butyrolactone with ethylene carbonate and diethyl carbonate; γ-butyrolactone with propylene carbonate; γ-butyrolactone with propylene carbonate and dimethyl carbonate; γ-butyrolactone with propylene carbonate and methyl ethyl carbonate; γ-butyrolactone with propylene carbonate and diethyl carbonate; γ-butyrolactone with ethylene carbonate and propylene carbonate; γ-butyrolactone with ethylene carbonate, propylene carbonate and dimethyl carbonate; γ-butyrolactone with ethylene carbonate, propylene carbonate and methyl ethyl carbonate; γ-butyrolactone with ethylene carbonate, propylene carbonate and diethyl carbonate; γ-butyrolactone with ethylene carbonate, dimethyl carbonate and methyl ethyl carbonate; γ-butyrolactone with ethylene carbonate, dimethyl carbonate and diethyl carbonate; γ-butyrolactone with ethylene carbonate, methyl ethyl carbonate and diethyl carbonate; γ-butyrolactone with ethylene carbonate, dimethyl carbonate, methyl ethyl carbonate, and diethyl carbonate; γ-butyrolactone with ethylene carbonate, propylene carbonate, dimethyl carbonate and methyl ethyl carbonate; γ-butyrolactone with ethylene carbonate, propylene carbonate, dimethyl carbonate and diethyl carbonate; γ-butyrolactone with ethylene carbonate, propylene carbonate, methyl ethyl carbonate, and diethyl carbonate; γ-butyrolactone with ethylene carbonate, propylene carbonate, dimethyl carbonate, methyl ethyl carbonate, and diethyl carbonate; γ-butyrolactone with sulfolane; γ-butyrolactone with ethylene carbonate and sulfolane; γ-butyrolactone with propylene carbonate and sulfolane; γ-butyrolactone with ethylene carbonate, propylene carbonate and sulfolane; and γ-butyrolactone with sulfolane and dimethyl carbonate.

[Other Solvents]

The non-aqueous electrolyte solution related to the invention may also include another solvent in addition to the solvents described above, as the non-aqueous solvent. Specific examples of the other solvent include amides such as dimethylformamide; acyclic carbamates such as methyl-N,N-dimethyl carbamate; cyclic amides such as N-methylpyrrolidone; cyclic ureas such as N,N-dimethylimidazolidinone; boron compounds such as trimethyl borate, triethyl borate, tributyl borate, trioctyl borate, and trimethylsilyl borate; and polyethylene glycol derivatives represented by the following formulas:

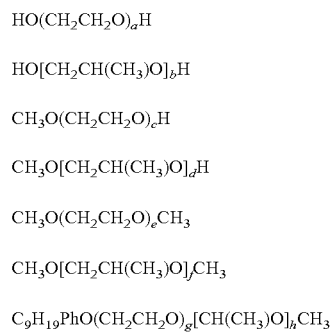

(Ph represents a phenyl group)

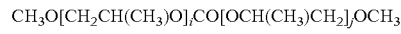

In the above formulas, a to f each represent an integer from 5 to 250; g to j each represent an integer from 2 to 249; $5 \leq g+h \leq 250$; and $5 \leq i+j \leq 250$.

[Electrolyte]

The non-aqueous electrolyte solution of the invention may include various known electrolytes, as long as they are normally used as electrolytes for a non-aqueous electrolyte solution.

Specific examples of the electrolyte include tetraalkyl ammonium salts such as $(C_2H_5)_4NPF_6$, $(C_2H_5)_4NBF_4$, $(C_2H_5)_4NClO_4$, $(C_2H_5)_4NAsF_6$, $(C_2H_5)_4N_2SiF_6$, $(C_2H_5)_4NOSO_2C_kF_{(2k+1)}$ (k is an integer from 1 to 8), $(C_2H_5)_4NPF_n[C_kF_{(2k+1)}]_{(6-n)}$ (n is an integer from 1 to 5, and k is an integer from 1 to 8); and lithium salts such as $LiPF_6$, $LiBF_4$, $LiClO_4$, $LiAsF_6$, $Li_2SiF_6$, $LiOSO_2C_kF_{(2k+1)}$ (k is an integer from 1 to 8), and $LiPF_n[C_kF_{(2k+1)}]_{(6-n)}$ (n is an integer from 1 to 5, k is an integer from 1 to 8). In addition, the lithium salt represented by the following formula may also be used.

$LiC(SO_2R^a)(SO_2R^b)(SO_2R^c)$, $LiN(SO_2OR^d)(SO_2OR^e)$, $LiN(SO_2R^f)(SO_2R^g)$ (wherein $R^a$, $R^b$, $R^c$, $R^d$, $R^e$, $R^f$, and $R^g$ may be identical or different, and are perfluoroalkyl groups having 1 to 8 carbon atoms). These electrolytes may be used singly, or two or more kinds may be used as mixtures.

Among them, lithium salts are particularly preferred, and $LiPF_6$, $LiBF_4$, $LiOSO_2C_kF_{(2k+1)}$ (k is an integer from 1 to 8), $LiClO_4$, $LiAsF_6$, $LiNSO_2[C_kF_{(2k+1)}]_2$ (k is an integer from 1 to 8), and $LiPF_n[C_kF_{(2k+1)}]_{(6-n)}$ (n is an integer from 1 to 5, and k is an integer from 1 to 8) are even more preferred.

In the invention, the normal concentration of the electrolyte in the non-aqueous electrolyte is normally from 0.1 mol/L to 3 mol/L, and preferably from 0.5 mol/L to 2 mol/L.

It is particularly preferred that the non-aqueous electrolyte solution of the invention contain $LiPF_6$. Since $LiPF_6$ has a high degree of dissociation, it increases the conductivity of the electrolyte solution, and inhibits the reduction decomposition reaction of the electrolyte solution on the negative electrode. $LiPF_6$ may be used alone, or in combination with other electrolyte. The other electrolyte may be any one as long as it is normally used as an electrolyte for a non-aqueous electrolyte solution, but is preferably a lithium salt other than $LiPF_6$ included in the above-described specific examples of the lithium salt.

Specific examples include: $LiPF_6$ and $LiBF_4$; $LiPF_6$ and $LiN[SO_2C_kF_{(2k+1)}]_2$ (k is an integer from 1 to 8); and $LiPF_6$, $LiBF_4$, and $LiN[SO_2C_kF_{(2k+1)}]$ (k is an integer from 1 to 8).

The proportion of the $LiPF_6$ in the lithium salt is preferably from 1% by mass to 100% by mass, more preferably from 10% by mass to 100% by mass, and even more preferably from 50% by mass to 100% by mass. The concentration of the electrolyte in the non-aqueous electrolyte solution is from 0.1 mol/L to 3 mol/L, and preferably from 0.5 mol/L to 2 mol/L.

[Compound Represented by Formula (IV)]

The non-aqueous electrolyte solution of the invention may contain a compound represented by formula (IV). The inclusion of the compound represented by formula (IV) in the non-aqueous electrolyte solution of the invention is preferred for the formation of a passivation film on the negative electrode.

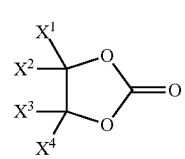

(IV)

In formula (IV), $Y^1$ and $Y^2$ each independently represent a hydrogen atom, a methyl group, an ethyl group, or a propyl group.

Examples of the compound represented by formula (IV) include vinylene carbonate, methylvinylene carbonate, ethyl vinylene carbonate, propyl vinylene carbonate, dimethylvinylene carbonate, diethylvinylene carbonate, and dipropylvinylene carbonate. Among them, vinylene carbonate is most preferred.

When the non-aqueous electrolyte solution of the invention contains the compound represented by formula (IV), the compound represented by formula (IV) may be used alone or in combination of two or more thereof. When the non-aqueous electrolyte solution of the invention contains the compound represented by formula (IV), the content of the compound represented by formula (IV) may be appropriately selected according to the intended use, but is preferably from 0.001% by mass to 10% by mass, and even more preferably from 0.05% by mass to 5% by mass relative to the total mass of the non-aqueous electrolyte solution.

In addition, when the non-aqueous electrolyte solution of the invention contains the compound represented by formula (IV), the content of the phosphonosulfonic acid compound represented by formula (I) is preferably from 0.001% by mass to 10% by mass, and more preferably from 0.05% by mass to 5% by mass relative to the total mass of the non-aqueous electrolyte solution. Within this range, a balance between an improvement in the low temperature discharge characteristics of a battery and an improvement in the storage characteristics of the battery can be achieved more effectively.

[Compound Represented by Formula (V)]

The non-aqueous electrolyte solution of the invention may contain a compound represented by formula (V). Inclusion of the compound represented by formula (V) in the non-aqueous electrolyte solution of the invention is preferred for the formation of a passivation film on the negative electrode.

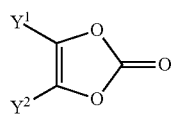

(V)

In formula (V), $X^1$, $X^2$, $X^3$ and $X^4$ each independently represent a vinyl group; an alkyl group having 1 to 3 carbon atoms, which may be substituted with a fluorine atom; a hydrogen atom; a fluorine atom; or a chlorine atom; provided that $X^1$, $X^2$, $X^3$ and $X^4$ are not all hydrogen atoms at the same time.

In formula (V), when $X^1$, $X^2$, $X^3$ and $X^4$ each represent an alkyl group having 1 to 3 carbon atoms which may be substituted with a fluorine atom, examples of the alkyl group having 1 to 3 carbon atoms which may be substituted with a fluorine atom include a fluoromethyl group, a difluoromethyl group, a trifluoromethyl group, a pentafluoroethyl group, and a heptafluoropropyl group.

The compound represented by formula (V) may be a known one, and examples thereof include vinyl ethylene carbonate; fluorinated ethylene carbonates wherein 1 to 4 hydrogen atoms of ethylene carbonate are substituted with fluorine, such as 4-fluoroethylene carbonate, 4,4-difluoroethylene carbonate, 4,5-difluoroethylene carbonate, 4,4,5-trifluoroethylene carbonate, and 4,4,5,5-tetrafluoroethylene carbonate. Among them, vinylethylene carbonate, 4,5-difluoroethylene carbonate, and 4-fluoroethylene carbonate are most preferred.

When the non-aqueous electrolyte solution of the invention contains the compound represented by formula (V), the compound represented by formula (V) may be used alone or in combination of two or more thereof.

When the non-aqueous electrolyte solution of the invention contains the compound represented by formula (V), the content of the compound represented by formula (V) may be appropriately selected according to the intended use, but is preferably from 0.001% by mass to 10% by mass, and even more preferably from 0.05% by mass to 5% by mass relative to the total mass of the non-aqueous electrolyte solution.

The non-aqueous electrolyte solution of the invention may contain both of the compound represented by formula (IV) and the compound represented by formula (V), and the preferred total content of them is the same as the above-described preferred content.

When the non-aqueous electrolyte solution of the invention contains the compound represented by formula (V), the content of the phosphonosulfonic acid compound represented by formula (I) is preferably from 0.001% by mass to 10% by mass, and more preferably from 0.05% by mass to 5% by mass relative to the total mass of the non-aqueous electrolyte solution. Within this range, a balance between an improvement in the low temperature discharge characteristics of a battery and an improvement in the storage characteristics of the battery can be achieved more effectively.

[Compound Represented by Formula (VI)]

The non-aqueous electrolyte solution of the invention may contain a compound represented by formula (VI). Inclusion of the compound represented by formula (VI) in the non-aqueous electrolyte solution of the invention is preferred for the formation of a passivation film on the negative electrode preferably. The compound represented by formula (VI) is a cyclic sulfate compound. The compound represented by formula (VI) may be hereinafter referred to as "the cyclic sulfate compound represented by formula (VI)".

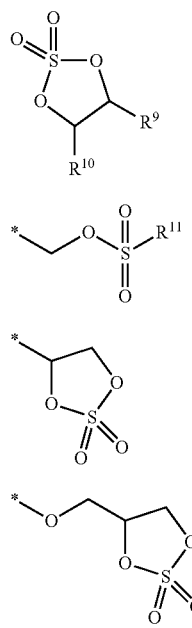

In formula (VI), $R^9$ and $R^{10}$ each independently represent a hydrogen atom, an alkyl group having 1 to 6 carbon atoms, a group represented by formula (VII), or a group represented by formula (VIII).

In formula (VII), $R^{11}$ represents a halogen atom, an alkyl group having 1 to 6 carbon atoms, a haloalkyl group having 1 to 6 carbon atoms, an alkoxy group having 1 to 6 carbon atoms, or a group represented by formula (IX).

In formulae (VII), (VIII), and (IX), * represents a position of bonding.

When the compound represented by formula (VI) contains two groups represented by formula (VII), the two groups represented by formula (VII) may be identical or different.

In formula (VI) (specifically in formula (VII)), specific examples of the "halogen atom" include a fluorine atom, a chlorine atom, a bromine atom, and an iodine atom.

In formula (VI) (specifically in formula (VII)), the halogen atom is preferably a fluorine atom.

In formula (VI), the "alkyl group having 1 to 6 carbon atoms" is the same as the "alkyl group having 1 to 6 carbon atoms" in formula (I), and specific examples of them are the same.

In formula (VI), the alkyl group having 1 to 6 carbon atoms is more preferably an alkyl group having 1 to 3 carbon atoms.

In formula (VI), the "haloalkyl group having 1 to 6 carbon atoms" is the same as the "haloalkyl group having 1 to 6 carbon atoms" in formula (I), specific examples of them are the same.

In formula (VI), the haloalkyl group having 1 to 6 carbon atoms is more preferably a haloalkyl group having 1 to 3 carbon atoms.

In formula (VI), the "alkoxy group having 1 to 6 carbon atoms" is a linear or branched alkoxy group having 1 to 6 carbon atoms, and specific examples thereof include a methoxy group, an ethoxy group, a propoxy group, an isopropoxy group, a butoxy group, an isobutoxy group, a sec-butoxy group, a tert-butoxy group, a pentyloxy group, a 2-methylbutoxy group, a 1-methylpentyloxy group, a neopentyloxy group, a 1-ethylpropoxy group, a hexyloxy group, and a 3,3-dimethylbutoxy group.

The alkoxy group having 1 to 6 carbon atoms is more preferably an alkoxy group having 1 to 3 carbon atoms.

In formula (VI), $R^9$ is preferably a hydrogen atom, an alkyl group having 1 to 3 carbon atoms, the group represented by formula (VII) (in formula (VII), $R^{11}$ is preferably a fluorine atom, an alkyl group having 1 to 3 carbon atoms, a haloalkyl group having 1 to 3 carbon atoms, an alkoxy group having 1 to 3 carbon atoms, or the group represented by formula (IX)), or the group represented by formula (VIII).

In formula (VI), $R^{10}$ is preferably a hydrogen atom, an alkyl group having 1 to 3 carbon atoms, the group represented by formula (VII) (in formula (VII), $R^{11}$ is preferably a fluorine atom, an alkyl group having 1 to 3 carbon atoms, a haloalkyl group having 1 to 3 carbon atoms, an alkoxy group having 1 to 3 carbon atoms, or the group represented by formula (IX)), or the group represented by formula (VIII), more preferably a hydrogen atom or a methyl group, and particularly preferably a hydrogen atom.

When $R^9$ in formula (VI) is the group represented by formula (VII), $R^{11}$ in formula (VII) is, as described above, a halogen atom, an alkyl group having 1 to 6 carbon atoms, a haloalkyl group having 1 to 6 carbon atoms, an alkoxy group having 1 to 6 carbon atoms, or the group represented by formula (IX), more preferably a fluorine atom, an alkyl group having 1 to 3 carbon atoms, a haloalkyl group having 1 to 3 carbon atoms, an alkoxy group having 1 to 3 carbon atoms, or the group represented by formula (IX), and more preferably a fluorine atom, a methyl group, an ethyl group, a methoxy group, an ethoxy group, or the group represented by formula (IX).

When $R^{10}$ in formula (VI) is the group represented by formula (VII), the preferred range of $R^{11}$ in formula (VII) is the same as the preferred range of $R^{11}$ when $R^9$ in formula (VI) is the group represented by formula (VII).

According to the preferred combination of $R^9$ and $R^{10}$ in formula (VI), $R^9$ is a hydrogen atom, an alkyl group having 1 to 3 carbon atoms, the group represented by formula (VII) (in formula (VII), $R^{11}$ is preferably a fluorine atom, an alkyl group having 1 to 3 carbon atoms, a haloalkyl group having 1 to 3 carbon atoms, an alkoxy group having 1 to 3 carbon atoms, or the group represented by formula (IX)), or the group represented by formula (VIII), $R^{10}$ is a hydrogen atom, an alkyl group having 1 to 3 carbon atoms, the group represented by formula (VII) (in formula (VII), $R^{11}$ is preferably a fluorine atom, an alkyl group having 1 to 3 carbon atoms, a haloalkyl group having 1 to 3 carbon atoms, an alkoxy group having 1 to 3 carbon atoms, or the group represented by formula (IX)), or the group represented by formula (VIII).

In formula (VI), according to the more preferred combination of $R^9$ and $R^{10}$, $R^9$ is a hydrogen atom, an alkyl group having 1 to 3 carbon atoms, the group represented by formula (VII) (in formula (VII), $R^{11}$ is preferably a fluorine atom, a methyl group, an ethyl group, a methoxy group, an ethoxy group, or the group represented by formula (IX)), or the group represented by formula (VIII), and $R^{10}$ is a hydrogen atom or a methyl group.

In formula (VI), according to the particularly preferred combination of $R^9$ and $R^{10}$, in formula (VI), $R^9$ is the group represented by formula (VIII), and $R^{10}$ is a hydrogen atom (most preferably 1,2:3,4-di-O-sulfanyl-meso-erythritol).

In formula (VI), the compound wherein $R^9$ is the group represented by formula (VII) is represented by the following formula (XV).

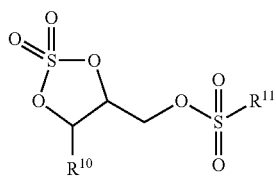

(XV)

In formula (XV), $R^{10}$ and $R^{11}$ are the same as $R^{10}$ and $R^{11}$ in formulae (VI) and (VII), respectively.

The compound represented by formula (XV) is preferably a compound wherein $R^{10}$ is a hydrogen atom or an alkyl group having 1 to 6 carbon atoms, $R^{11}$ is a halogen atom, an alkyl group having 1 to 6 carbon atoms, a haloalkyl group having 1 to 6 carbon atoms, an alkoxy group having 1 to 6 carbon atoms, or the group represented by formula (IX).

Furthermore, the compound represented by formula (XV) is particularly preferably a compound wherein $R^{10}$ is a hydrogen atom or a methyl group, $R^{11}$ is a fluorine atom, a methyl group, an ethyl group, a methoxy group, an ethoxy group, or the group represented by formula (IX).

The compound represented by formula (VI) is preferably 2,2-dioxo-1,3,2-dioxathiolane, 4-methyl-2,2-dioxo-1,3,2-dioxathiolane, 4-ethyl-2,2-dioxo-1,3,2-dioxathiolane, 4-propyl-2,2-dioxo-1,3,2-dioxathiolane, 4-methylsulfonyloxymethyl-2,2-dioxo-1,3,2-dioxathiolane, 4-ethylsulfonyloxymethyl-2,2-dioxo-1,3,2-dioxathiolane, bis((2,2-dioxo-1,3,2-dioxathiolane-4-yl)methyl) sulfate, 1,2:3,4-di-O-sulfanyl-meso-erythritol, or 1,2:3,4-di-O-sulfanyl-D,L-threitol, more preferably, 2,2-dioxo-1,3,2-dioxathiolane, 4-methyl-2,2-dioxo-1,3,2-dioxathiolane, 4-ethyl-2,2-dioxo-1,3,2-dioxathiolane, 4-propyl-2,2-dioxo-1,3,2-dioxathiolane, 4-methylsulfonyloxymethyl-2,2-dioxo-1,3,2-dioxathiolane, 4-ethylsulfonyloxymethyl-2,2-dioxo-1,3,2-dioxathiolane, bis((2,2-dioxo-1,3,2-dioxathiolane-4-yl) methyl) sulfate, or 1,2:3,4-di-O-sulfanyl-meso-erythritol, and particularly preferably 2,2-dioxo-1,3,2-dioxathiolane, 4-methyl-2,2-dioxo-1,3,2-dioxathiolane, 4-ethyl-2,2-dioxo-1,3,2-dioxathiolane, 4-propyl-2,2-dioxo-1,3,2-dioxathiolane, 4-methylsulfonyloxymethyl-2,2-dioxo-1,3,2-dioxathiolane, 4-ethylsulfonyloxymethyl-2,2-dioxo-1,3,2-dioxathiolane, or bis((2,2-dioxo-1,3,2-dioxathiolane-4-yl) methyl) sulfate.

When the non-aqueous electrolyte solution of the invention contains the compound represented by formula (VI), the compound represented by formula (VI) may be used alone or in combination of two or more thereof.

When the non-aqueous electrolyte solution of the invention contains the compound represented by formula (VI), the content of the compound represented by formula (VI) may be appropriately selected according to the intended use, but is preferably from 0.001% by mass to 10% by mass, and even more preferably from 0.05% by mass to 5% by mass relative to the total mass of the non-aqueous electrolyte solution.

When the non-aqueous electrolyte solution of the invention contains the compound represented by formula (VI), the content of the phosphonosulfonic acid compound represented by formula (I) is preferably from 0.001% by mass to 10% by mass, and more preferably from 0.05% by mass to 5% by mass relative to the total mass of the non-aqueous electrolyte solution. Within this range, a balance between an improvement in the low temperature discharge characteristics of a battery and an improvement in the storage characteristics of the battery can be achieved more effectively.

[Lithium Difluorophosphate, Compound Represented by Formula (X), (XI), or (XII)]

The non-aqueous electrolyte solution of the invention preferably further contains at least one compound selected from the group consisting of lithium difluorophosphate (LiOP(O)F$_2$), a compound represented by formula (X), a compound represented by formula (XI), and a compound represented by formula (XII), thereby more effectively achieving the effect of the invention.

The at least one compound selected from the group is an electrolyte compound.

The at least one compound selected from the group may be hereinafter referred to as "specific electrolyte compound".

The electrolyte in the non-aqueous electrolyte solution of the invention may be, by itself, an electrolyte other than the specific electrolyte compound (for example, the above-described general electrolyte), the specific electrolyte compound by itself, or a combination of the specific electrolyte compound and an electrolyte other than the specific electrolyte compound.

In particular, when the non-aqueous electrolyte solution of the invention contains the specific electrolyte and an electrolyte other than the specific electrolyte compound, electric conductivity, which is a basic feature of an electrolyte for a common non-aqueous electrolyte solution, is maintained, and the battery performance (in particular low temperature discharge characteristics of the battery at the initial stage and during storage in a charged state) are further improved. In addition, when at least one of the specific electrolyte compound or the electrolyte other than the specific electrolyte compound contains a lithium ion, the at least one of the specific electrolyte compound or the electrolyte other than the specific electrolyte compound is a stable source of lithium ions.

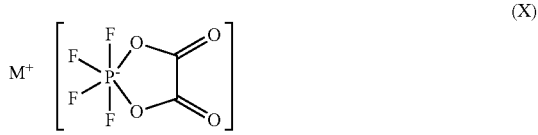

(X)

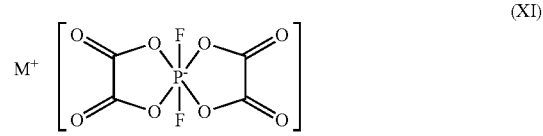

(XI)

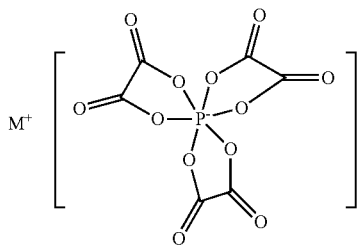

(XII)

In formulae (X), (XI), and (XII), M is an alkali metal.

The M is preferably lithium, sodium, or potassium, and more preferably lithium.

In regard to the method for synthesizing the electrolyte compound represented by formula (X), (XI), or (XII), for example, in the case of a compound represented by formula (X), a method of causing $LiPF_6$ to react with oxalic acid in a one-fold molar amount of this $LiPF_6$ in a non-aqueous solvent, thereby substituting the fluorine atoms linked to phosphorus with the oxalic acid, may be used.

Furthermore, in the case of a compound represented by formula (XI), a method of causing $LiPF_6$ to react with oxalic acid in a two-fold molar amount of this $LiPF_6$ in a non-aqueous solvent, thereby substituting the fluorine atoms linked to phosphorus with the oxalic acid, may be used.

Furthermore, in the case of a compound represented by formula (XII), a method of causing $LiPF_6$ to react with oxalic acid in a three-fold molar amount of this $LiPF_6$ in a non-aqueous solvent, thereby substituting the fluorine atoms linked to phosphorus with the oxalic acid, may be used.

In these cases, lithium salts of the anion compounds can be obtained.

When the non-aqueous electrolyte solution of the invention contains at least one compound selected from the group consisting of lithium difluorophosphate, the compound represented by formula (X), the compound represented by formula (XI), and the compound represented by formula (XII), the total content of lithium difluorophosphate, the compound represented by formula (X), the compound represented by formula (XI), and the compound represented by formula (XII) is preferably from 0.001% by mass to 10% by mass, and more preferably from 0.05% by mass to 5% by mass relative to the total mass of the non-aqueous electrolyte solution. Within this range, a balance between an improvement in the low temperature discharge characteristics of a battery and an improvement in the storage characteristics of the battery can be achieved more effectively.

In addition, when the non-aqueous electrolyte solution of the invention contains at least one compound selected from the group consisting of lithium difluorophosphate, the compound represented by formula (X), the compound represented by formula (XI), and the compound represented by formula (XII), the content of the phosphonosulfonic acid compound represented by formula (I) is preferably from 0.001% by mass to 10% by mass, and more preferably from 0.05% by mass to 5% by mass relative to the total mass of the non-aqueous electrolyte solution. Within this range, a balance between an improvement in the low temperature discharge characteristics of a battery and an improvement in the storage characteristics of the battery can be achieved more effectively.

The non-aqueous electrolyte solution of the invention is not only suitable as a non-aqueous electrolyte solution for lithium secondary batteries, but can also be used as a non-aqueous electrolyte solution for primary batteries, a non-aqueous electrolyte solution for electrochemical capacitors, or an electrolyte solution for electric double layer capacitors or aluminum electrolytic capacitors.

<Lithium Secondary Battery>

The lithium secondary battery of the invention is constituted to basically include a negative electrode, a positive electrode, and the non-aqueous electrolyte solution of the invention, and usually, a separator is provided between the negative electrode and the positive electrode.

(Negative Electrode)

As the negative electrode active material that constitutes the negative electrode, at least one selected from metal lithium, a lithium-containing alloy, a metal or alloy capable of alloying with lithium, an oxide capable of doping and dedoping of lithium ions, transition metal nitrides capable of doping and dedoping of lithium ions, and a carbon material capable of doping and dedoping of lithium ions (these may be used singly, or mixtures including two or more kinds of these may also be used) can be used.

Examples of the metal or alloy capable of alloying with lithium (or lithium ions) include silicon, a silicon alloy, tin, and a tin alloy. Furthermore, lithium titanate is also acceptable.

Among these, a carbon material capable of doping and dedoping of lithium ions is preferred. Examples of such a carbon material include carbon black, activated carbon, a graphite material (artificial graphite or natural graphite), and an amorphous carbon material. The form of the carbon material may be any of a fibrous form, a spherical form, a potato form and a flake form.

Specific examples of the amorphous carbon material include hard carbon, cokes, mesocarbon microbeads (MCMB) calcined at or below 1500° C., and mesophase pitch carbon fibers (MCF).

Examples of the graphite material include natural graphite and artificial graphite. Regarding the artificial graphite, graphitized MCMB, graphitized MCF, and the like are used. Furthermore, compounds containing boron can also be used as the graphite material. Also, as the graphite material, a graphite material coated with a metal such as gold, platinum, silver, copper or tin; a graphite material coated with an amorphous carbon; or a mixture of amorphous carbon and graphite can also be used.

These carbon materials may be used singly, or two or more kinds may also be used as mixtures.

The carbon material is particularly preferably a carbon material in which the interplanar spacing d(002) of the (002) plane measured by an X-ray analysis is 0.340 nm or less. Furthermore, the carbon material is also preferably a graphite having a true density of 1.70 g/cm³ or greater, or a highly crystalline carbon material having properties close thereto. When a carbon material such as described above is used, the energy density of the battery can be further increased.

(Positive Electrode)

Examples of the positive electrode active material that constitutes the positive electrode include transition metal oxides or transition metal sulfides, such as $MoS_2$, $TiS_2$, $MnO_2$, and $V_2O_5$; composite oxides composed of lithium and transition metals, such as $LiCoO_2$, $LiMnO_2$, $LiMn_2O_4$, $LiNiO_2$, $LiNi_xCo_{(1-x)}O_2$ [0<X<1], and $LiFePO_4$; and electroconductive polymer materials such as polyaniline, polythiophene, polypyrrole, polyacetylene, polyacene, dimercaptothiadiazole, and a polyaniline composite. Among these, composite oxides composed of lithium and transition metals are particularly preferred. When the negative electrode is formed of lithium metal or a lithium alloy, a carbon material can be used as the positive electrode. Also, a mixture of a composite oxide of lithium and a transition metal with a carbon material can be used as the positive electrode.

The positive electrode active materials described above may be used singly, or two or more kinds may also be used as mixtures. If the positive electrode active material has insufficient electroconductivity, the positive electrode can be constructed by using the positive electrode active material together with an electroconductive aid. Examples of the electroconductive aid include carbon materials such as carbon black, amorphous whiskers, and graphite.

(Separator)

The separator is a membrane which electrically insulates the positive electrode and the negative electrode, and transmits lithium ions, and examples thereof include a porous film and a polymer electrolyte.

As the porous film, a finely porous polymer film is suitably used, and examples of materials of the porous film include polyolefins, polyimides, polyvinylidene fluoride, and polyesters.

Particularly, porous polyolefins are preferred, and specific examples thereof include a porous polyethylene film, a porous polypropylene film, and a multilayer film of a porous polyethylene film and a porous polypropylene film. A porous polyolefin film may also have another resin with excellent thermal stability coated thereon.

Examples of the polymer electrolyte include a polymer having a lithium salt dissolved therein, and a polymer swollen with an electrolyte solution.

The non-aqueous electrolyte solution of the invention may also be used for the purpose of obtaining a polymer electrolyte by swelling a polymer.

(Configuration of Battery)

The lithium secondary battery of the invention includes the negative electrode active material, positive electrode active material, and separator described above.

The lithium secondary battery of the invention can adopt various known shapes, and the lithium secondary battery can be formed into a cylindrical shape, a coin shape, a rectangular shape, a film shape, and any other shapes. However, the basic structure of the battery is the same irrespective of the shape, and modifications in design can be applied in accordance with the purpose.

An example of the non-aqueous electrolyte secondary battery of the invention may be a coin battery as illustrated in FIG. 1.

In the coin battery illustrated in FIG. 1, a disc-shaped negative electrode 2, a separator 5 in which a non-aqueous electrolyte solution obtained by dissolving an electrolyte in a non-aqueous solvent has been injected, a disc-shaped positive electrode 1, and optionally, spacer plates 7 and 8 made of stainless steel, aluminum or the like, which are laminated in this order, are accommodated between a positive electrode can 3 (hereinafter, also referred to as a "battery can") and a sealing plate 4 (hereinafter, also referred to as a "battery can lid"). The positive electrode can 3 and the sealing plate 4 are sealed by caulking with a gasket 6.

Meanwhile, the lithium secondary battery of the invention may be a lithium secondary battery obtained by charging and discharging a lithium secondary battery (a lithium secondary battery before being charged and discharged) which includes a negative electrode, a positive electrode, and the non-aqueous electrolyte solution of the invention.

That is, the lithium secondary battery of the invention may be a lithium secondary battery (a lithium secondary battery that has been charged and discharged) obtained by first producing a lithium secondary battery before being charged and discharged, which includes a negative electrode, a positive electrode and the non-aqueous electrolyte solution of the invention, and subsequently charging and discharging one or more times the lithium secondary battery before being charged and discharged.

There are no particular limitations on the use of the non-aqueous electrolyte solution of the invention, and of a lithium secondary battery using the non-aqueous electrolyte solution, and the non-aqueous electrolyte solution and the secondary battery can be used in various known applications. For example, the non-aqueous electrolyte solution and the secondary battery can be widely utilized in small-sized portable devices as well as in large-sized devices, such as notebook computers, mobile computers, mobile telephones, headphone stereos, video movie cameras, liquid crystal television sets, handy cleaners, electronic organizers, calculators, radios, back-up power supply applications, motors, automobiles, electric cars, motorcycles, electric motorcycles, bicycles, electric bicycles, illuminating devices, game players, time pieces, electric tools, and cameras.

EXAMPLES

The invention is more specifically described below with reference to the following examples, but the invention will not be limited by these examples. In the following examples, "%" or "wt %" means % by mass.

The synthesis example of the phosphonosulfonic acid compound represented by formula (I) is shown below.

Synthesis Example 1

Synthesis of Methyl Diethyl Phosphonomethanesulfonate (Exemplary Compound 10)

Methyl methanesulfonate (5.00 g, 45.4 mmol) was dissolved in tetrahydrofuran (100 ml), n-butyl lithium (1.6 M hexane solution, 31 ml, 49.9 mmol) was dropped into the solution under cooling at −78° C., and stirred for 30 minutes at this temperature. Subsequently, diethylphosphoric acid chloride (3.9 ml, 27.2 mmol) was dropped into the solution, and stirred at −78° C. for 1 hour, and at −50° C. for 30 minutes. A saturated ammonium chloride aqueous solution was added to the reaction liquid and stirred, the mixture was further diluted with water, and then extracted with ethyl acetate twice. The combined extract (organic layer) was washed with water and a saturated saline solution, dried with anhydrous magnesium sulfate, and then concentrated. The oily object thus obtained was purified by silica gel column chromatography (ethyl acetate/hexane system), and thus 5.04 g (yield 75%) of methyl diethyl phosphonomethanesulfonate (exemplary compound 10) was obtained. The NMR result of the compound thus obtained was as follows.

$^1$H-NMR (270 MHz, CDCl$_3$) δ (ppm): 4.31-4.20 (4H, m), 3.73 (2H, d, J=17.5 Hz), 1.42-1.35 (6H, m).

Synthesis Example 2

Synthesis of Trimethylsilyl Bis(Trimethylsilyl) Phosphonomethanesulfonate (Exemplary compound 23)

Methyl diethyl phosphonomethanesulfonate (exemplary compound 10) (5.04 g, 20.5 mmol) was dissolved in methylene chloride (25 ml), and trimethylsilyl bromide (10.8 ml, 80.9 mmol) was added at room temperature. After stirring at room temperature for 6 hours, the reaction liquid was concentrated under reduced pressure, and thus trimethylsilyl bis(trimethylsilyl) phosphonomethanesulfonate (exemplary compound 23) was obtained (7.67 g, yield 95%). The NMR result of the compound thus obtained was as follows.

$^1$H-NMR (270 MHz, CDCl$_3$) δ (ppm): 3.90 (2H, d, J=18.4 Hz), 0.36 (18H, s), 0.07 (9H, s).

Synthesis Example 3

Synthesis of Trimethylsilylmethyl Bis(Trimethylsilylmethyl) Phosphonomethanesulfonate (Exemplary Compound 71)

(Process 1)

In accordance with the method described in Chemische Berichte, 1980, Vol. 113, (1), 142-151, 13.08 g (47%) of (dichlorophosphoryl)methanesulfonyl chloride was obtained from phosphonoacetic acid (16.8 g).

(Process 2)

Trimethylsilyl methanol (0.9 ml, 7.13 mmol) and triethylamine (1.5 ml, 10.8 mmol) were dissolved in methylene chloride (20 ml) to make a solution, to which a solution of the above-described (dichlorophosphoryl)methanesulfonyl chloride (0.50 g, 2.16 mmol) in methylene chloride (2 ml) was added under cooling with ice. After stirring for 2 hours under cooling with ice, the reaction liquid was poured into water. The mixture was extracted with methylene chloride. The combined extract (organic layer) was washed with a saturated saline solution, dried with anhydrous magnesium sulfate, and concentrated under reduced pressure. The crude product thus obtained was purified by silica gel chromatography, and thus trimethylsilylmethyl bis(trimethylsilylmethyl) phosphonomethanesulfonate (exemplary compound 71) (58.1 mg, yield 6%) was obtained. The NMR result of the compound thus obtained was as follows.

$^1$H-NMR (270 MHz, CDCl$_3$) δ (ppm): 3.99 (2H, s), 3.85 (2H, d, J=6.3 Hz), 3.67 (2H, d, J=16.8 Hz), 0.15 (9H, s), 0.12 (18H, s).

Synthesis Example 4

Synthesis of Phosphonomethanesulfonic Acid (Exemplary Compound 1)

The trimethylsilyl bis(trimethylsilyl) phosphonomethanesulfonate obtained in Synthesis Example 2 (exemplary compound 23) (236.5 mg, 0.602 mmol) was dissolved in methanol (5 ml) and stirred at room temperature for 2 days. The reaction liquid was concentrated under reduced pressure, further dried using a vacuum pump, and thus phosphonomethanesulfonic acid (exemplary compound 1) (104.9 mg, yield 99%) was obtained. The NMR result of the compound thus obtained was as follows.

$^1$H-NMR (270 MHz, acetone-d$_6$) δ (ppm): 3.75 (2H, d, J=17.5 Hz).

Synthesis Example 5

Synthesis of Phenyl 2-(Diethoxyphosphoryl) Ethanesulfonate (Exemplary Compound 43)

Diethyl phosphite (0.90 g, 6.50 mmol) and diazabicycloundecene (0.99 g, 6.50 mmol) were dissolved in tetrahydrofuran (20 ml) to make a solution, to which a solution of phenyl vinyl sulfonate (1.14 g, 6.19 mmol) in tetrahydrofuran (3 ml) was dropped under cooling with ice. After stirring for 4 hours under cooling with ice, the reaction liquid was poured into water. The mixture was extracted with ethyl acetate twice. The combined extract (organic layer) was washed with a saturated saline solution, dried with anhydrous magnesium sulfate, and concentrated under reduced pressure. The crude product thus obtained was purified by silica gel chromatography, and thus phenyl 2-(diethoxyphosphoryl) ethanesulfonate (exemplary compound 43) (0.97 g, yield 49%) was obtained. The NMR result of the compound thus obtained was as follows.

$^1$H-NMR (270 MHz, CDCl$_3$) δ (ppm): 7.46-7.25 (5H, m), 4.21-4.09 (4H, m), 3.52-3.43 (2H, m), 2.45-2.31 (2H, m), 1.39-1.32 (6H, m).

Synthesis Example 6

Synthesis of Phenyl 2-(Hydroxy(Trimethylsilyloxy)Phosphoryl) Ethanesulfonate (Exemplary Compound 81)

The phenyl 2-(diethoxyphosphoryl) ethanesulfonate obtained in Synthesis Example 5 (exemplary compound 43) (726.3 mg, 2.25 mmol) was dissolved in methylene chloride (14.5 ml), and trimethylsilyl bromide (0.71 ml, 5.4 mmol) was added at room temperature. After stirring for 16 hours at room temperature, the reaction liquid was concentrated under reduced pressure, and thus phenyl 2-(hydroxy(trimethylsilyloxy)phosphoryl) ethanesulfonate (exemplary compound 81) (750.2 mg, yield 98%) was obtained. The NMR result of the compound thus obtained was as follows.

$^1$H-NMR (270 MHz, CDCl$_3$) δ (ppm): 7.46-7.24 (5H, m), 3.52-3.40 (2H, m), 2.47-2.30 (2H, m), 0.32 (9H, s).

The synthesis examples of the exemplary compounds 10, 23, 71, 1, 43, and 81 are described above as the synthesis example of the phosphonosulfonic acid compound represented by formula (I), but other phosphonosulfonic acid compounds represented by formula (I) can be synthesized by similar methods as the above synthesis examples.

Example 1

A lithium secondary battery was made by the following procedure.

<Preparation of Negative Electrode>

20 parts by mass of artificial graphite, 80 parts by mass of natural graphite-based graphite, 1 part by mass of carboxymethyl cellulose, and 2 parts by mass of a SBR latex were kneaded in water solvent, and thus a negative electrode mixture slurry in a paste form was prepared.

Next, this negative electrode mixture slurry was applied on a strip-shaped negative electrode current collector made of a copper foil having a thickness of 18 μm, and the slurry was dried. Subsequently, the assembly was compressed with a roll press, and thus a sheet-like negative electrode composed of a negative electrode current collector and a negative electrode active material layer was obtained. The coating density of the negative electrode active material layer in this case was 10 mg/cm$^2$, and the packing density was 1.5 g/ml.

<Preparation of Positive Electrode>

90 parts by mass of LiCoO$_2$, 5 parts by mass of acetylene black, and 5 parts by mass of polyvinylidene fluoride were kneaded in N-methylpyrrolidinone as a solvent, and thus a positive electrode mixture slurry in a paste form was prepared.

Next, this positive electrode mixture slurry was applied on a strip-shaped positive electrode current collector made of an aluminum foil having a thickness of 20 μm, and the slurry was dried. Subsequently, the assembly was compressed with a roll press, and thus a sheet-like positive electrode composed of a positive electrode current collector and a positive electrode active material layer was obtained. The coating density of the positive electrode active material layer in this case was 30 mg/cm$^2$, and the packing density was 2.5 g/ml.

<Preparation of Non-Aqueous Electrolyte Solution>

In a mixture of ethylene carbonate (EC), dimethyl carbonate (DMC) and methyl ethyl carbonate (EMC) at proportions of 34:33:33 (mass ratio) as a non-aqueous solvent, LiPF$_6$ as an electrolyte was dissolved such that the electrolyte concentration in the finally obtainable non-aqueous electrolyte solution would be 1 mol/liter.

To the solution thus obtained, the trimethylsilyl bis(trimethylsilyl) phosphonomethanesulfonate (exemplary compound 23) obtained in Synthesis Example 2 was added as an additive such that the content thereof relative to the total mass of the finally obtained non-aqueous electrolyte solution would be 0.5 wt %, and thus a non-aqueous electrolyte solution was obtained.

<Preparation of Coin Battery>

The negative electrode described above was punched into a disc form having a diameter of 14 mm, while the positive electrode described above was punched into a disc form having a diameter of 13 mm, and thus coin-shaped electrodes (a negative electrode and a positive electrode) were obtained. Furthermore, a finely porous polyethylene film having a thickness of 20 μm was punched into a disc form having a diameter of 17 mm, and thus a separator was obtained.

The coin-shaped negative electrode, the separator and the coin-shaped positive electrode thus obtained were laminated in this order inside a battery can (size 2032) made of stainless steel, and 20 μl of a non-aqueous electrolyte solution was injected therein to impregnate the separator, the positive electrode, and the negative electrode.

Furthermore, an aluminum plate (thickness: 1.2 mm, diameter: 16 mm) and a spring were mounted on the positive electrode, a gasket made of polypropylene was inserted, and the battery was sealed by caulking with the battery can lid. Thus, a coin type lithium secondary battery (hereinafter, may be referred to as a "coin battery" or a "test battery") having a diameter of 20 mm and a height of 3.2 mm and having the configuration illustrated in FIG. 1 was prepared.

The coin battery (a test battery) thus obtained was subjected to the following measurements.

[Evaluation Methods]

<Measurement of Resistance Value (−20° C.) as Initial Characteristic of Battery>

The coin battery was charged at a constant voltage of 4.0 V, then the charged coin battery was cooled to −20° C. in a constant temperature chamber, discharged at a constant current of 0.2 mA at −20° C., and the electric potential decrease in 10 seconds after initiation of discharge was measured, thereby determining the direct current resistance [Ω] of the coin battery, and the obtained value was recorded as the initial resistance value [Ω] (−20° C.). The initial resistance value [Ω] (−20° C.) of the coin battery of Comparative Example 1 described below was also measured in the same manner.

From these results, using the following formula, the "initial characteristic, resistance value (−20° C.) [%]", which is the initial resistance value (relative value; %) in Example 1 relative to the initial resistance value [Ω] (−20° C.) in Comparative Example 1 defined as 100%, was determined.

The obtained results are shown in Table 1.

Initial characteristic, resistance value (−20° C.) [%]= (initial resistance value [Ω](−20° C.) in Example 1/(initial resistance value [Ω] (−20° C.) in Comparative Example 1)×100[%]

<Measurement of Capacity Retention as Storage Characteristic of Battery>

The coin battery obtained above was charged at a constant current of 1 mA and a constant voltage of 4.2 V in a constant temperature chamber at 25° C., then discharged to 2.85 V at a constant current of 1 mA in the constant temperature chamber at 25° C., and the discharge capacity [mAh] of first cycle was measured.

Subsequently, the coin battery was charged at a constant voltage of 4.2 V, the charged coin battery was stored in a constant temperature chamber at 80° C. for 2 days (hereinafter this operation is referred to as "high temperature storage test"), then the discharge capacity [mAh] after the high temperature storage test was measured in the same manner for the discharge capacity of first cycle, and the capacity retention [%] as a storage characteristic of the battery was calculated by the following formula.

The results thus obtained are shown in Table 1.

Storage characteristic, capacity retention[%]=(discharge capacity [mAh] after high temperature storage test/discharge capacity [mAh] of first cycle)×100[%]

The capacity retention [%] of the coin battery in Comparative Example 1 described below was also calculated in the same manner.

From these results, the capacity retention (relative value; %) in Example 1 relative to the capacity retention in Comparative Example 1 defined as 100% was determined The capacity retention (relative value; %) thus obtained is shown in Table 1.

<Measurement of Resistance Value (−20° C.) as Storage Characteristic of Battery>

The coin battery after the measurement of the initial resistance value was charged at a constant voltage of 4.2 V, and the charged coin battery was stored for 2 days in a constant temperature chamber at 80° C. (high temperature storage test). Subsequently, the resistance value (−20° C.) of the coin battery after the high temperature storage test was measured in the same manner as the above-described initial resistance value (−20° C.). The resistance value (−20° C.) of the coin battery of Comparative Example 1 described below after the high temperature storage test was also measured in the same manner.

From these results, using the following formula, the "storage characteristics, resistance value (−20° C.) [%]" in Example 1, which is the resistance value (relative value; %) after the high temperature storage test in Example 1 relative to the resistance value [Ω] (−20° C.) in Comparative Example 1 defined as 100%, was determined.

The results thus obtained are shown in Table 1.

Storage characteristic, resistance value (−20° C.) [%]= (resistance value after high temperature storage test in Example 1 [Ω] (−20° C.)/resistance value after high temperature storage test in Comparative Example 1 [Ω] (−20° C.))×100[%]

Example 2

A coin battery was obtained in the same manner as in Example 1, except that in the preparation of the non-aqueous electrolyte solution in Example 1, the exemplary compound 71 was added in place of the exemplary compound 23 such that the content relative to the total mass of the finally obtained non-aqueous electrolyte solution would be 0.5 wt %.

The coin battery thus obtained was subjected to various measurements in the same manner as in Example 1. The evaluation results are shown in Table 1.

Example 3

A coin battery was obtained in the same manner as in Example 1, except that in the preparation of the non-aqueous electrolyte solution in Example 1, the exemplary compound 10 was added in place of the exemplary compound 23 such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 1.

Example 4

A coin battery was obtained in the same manner as in Example 1, except that in the same manner as in Example 1, except that in the preparation of the non-aqueous electrolyte solution in Example 1, the exemplary compound 1 was added in place of the exemplary compound 23 such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 1.

Example 5

A coin battery was obtained in the same manner as in Example 1, except that in the same manner as in Example 1, except that in the preparation of the non-aqueous electrolyte solution in Example 1, the exemplary compound 43 was added in place of the exemplary compound 23 such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 1.

Example 6

A coin battery was obtained in the same manner as in Example 1, except that in the same manner as in Example 1, except that in the preparation of the non-aqueous electrolyte solution in Example 1, the exemplary compound 81 was added in place of the exemplary compound 23 such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 1.

Comparative Example 1

A coin battery was obtained in the same manner as in Example 1, except that in the preparation of the non-aqueous electrolyte solution in Example 1, the additive (the exemplary compound 23) was not added.

The coin battery thus obtained was subjected to various measurements in the same manner as in Example 1. The evaluation results are shown in Table 1.

Comparative Example 2

A coin battery was obtained in the same manner as in Example 1, except that in the preparation of the non-aqueous electrolyte solution in Example 1, ethyl diethylphosphonomethane carboxylate (Comparative Compound 1) was added in place of the exemplary compound 23 such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 1.

TABLE 1

|  | Additive for non-aqueous electrolyte solution (0.5 wt %) | | Initial characteristics | Storage characteristics | |
|---|---|---|---|---|---|
|  | Formula (I) compound | Comparative compound | Resistance value (−20° C.) [%] | Capacity retention [%] | Resistance value (−20° C.) [%] |
| Example 1 | Exemplary compound 23 | None | 89 | 101 | 78 |
| Example 2 | Exemplary compound 71 | None | 91 | 98 | 77 |
| Example 3 | Exemplary compound 10 | None | 95 | 100 | 76 |
| Example 4 | Exemplary compound 1 | None | 96 | 99 | 72 |
| Example 5 | Exemplary compound 43 | None | 96 | 98 | 96 |
| Example 6 | Exemplary compound 81 | None | 88 | 98 | 95 |
| Comparative Example 1 | None | None | 100 | 100 | 100 |
| Comparative Example 2 | None | Comparative compound 1 | 110 | 92 | 102 |

In Table 1 shown above and Tables 2 and 3 shown below, the additive amount of the additive for non-aqueous electrolyte solution means % by mass (wt %) relative to the total mass of the finally obtained non-aqueous electrolyte solution.

In addition, in Table 1 shown above and Tables 2 and 3 shown below, the "formula (I) compound" means the phosphonosulfonic acid compound represented by formula (1).

The structures of the exemplary compounds used in the examples and comparative examples are shown below.

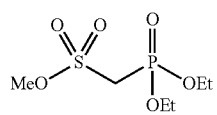

Exemplary compound 10

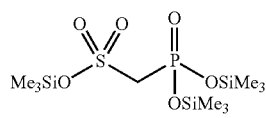

Exemplary compound 23

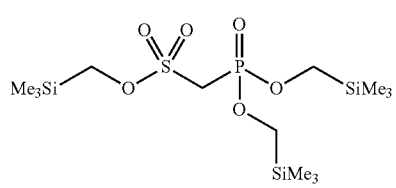

Exemplary compound 71

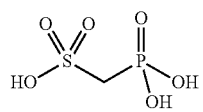

Exemplary compound 1

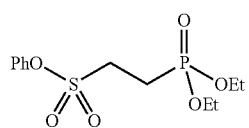

Exemplary compound 43

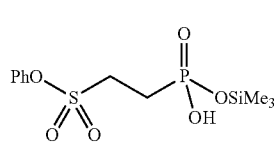

Exemplary compound 81

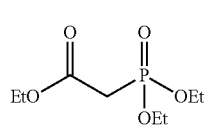

Comparative compound 1

As shown in Table 1, in Examples 1 to 6, the low temperature resistance value as one of the storage characteristics was significantly reduced with the capacity retention maintained, in comparison with Comparative Example 1 which contained no additive. In addition, in Examples 1 to 6, the low temperature resistance value as one of the initial characteristics was significantly reduced, in comparison with Comparative Example 1.

On the other hand, in Comparative Example 2 wherein Comparative Compound 1 was added, the storage characteristics were adversely affected by the addition of Comparative Compound 1, and the low temperature resistance value as one of the initial characteristics was tending higher.

Example 7

A coin battery was obtained in the same manner as in Example 1, except that in the preparation of the non-aqueous electrolyte solution in Example 1, vinylene carbonate (compound A) as an additive was further added such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 2.

Examples 8 to 13

In each example, a coin battery was obtained in the same manner as in Example 7, except that in the preparation of the non-aqueous electrolyte solution in Example 7, the compounds B to G were added respectively in place of vinylene carbonate (compound A) such that the content thereof relative to the total mass of the finally obtained non-aqueous electrolyte solution would be 0.5 wt % respectively.

The coin batteries thus obtained were subjected to various measurements in the same manner as in Example 1. The evaluation results are shown in Table 2.

Example 14

A coin battery was obtained in the same manner as in Example 3, except that in the preparation of the non-aqueous electrolyte solution in Example 3, vinylene carbonate (compound A) as an additive was further added such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 2.

Examples 15 to 20

In each example, a coin battery was obtained in the same manner as in Example 14, except that in the preparation of the non-aqueous electrolyte solution in Example 14, the compounds B to G were added respectively in place of vinylene carbonate (compound A) such that the content thereof relative to the total mass of the finally obtained non-aqueous electrolyte solution would be 0.5 wt % respectively.

The coin batteries thus obtained were subjected to various measurements in the same manner as in Example 1. The evaluation results are shown in Table 2.

Example 21

A coin battery was obtained in the same manner as in Example 4, except that in the preparation of the non-aqueous electrolyte solution in Example 4, the compound G as an additive was further added such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 2.

Example 22

A coin battery was obtained in the same manner as in Example 5, except that in the preparation of the non-aqueous electrolyte solution in Example 5, the compound G as an additive was further added such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 2.

Example 23

A coin battery was obtained in the same manner as in Example 6, except that in the preparation of the non-aqueous electrolyte solution in Example 6, the compound G as an additive was further added such that the content thereof relative to the total mass of the finally obtained non-aqueous electrolyte solution would be 0.5 wt %.

The coin battery thus obtained was subjected to various measurements in the same manner as in Example 1. The evaluation results are shown in Table 2.

For comparison, Table 2 also shows the results of Comparative Example 1 which have been shown in Table 1.

The structures of the compounds A to G used in the examples are shown below.

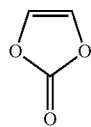

Compound A

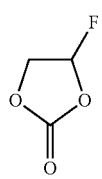

Compound B

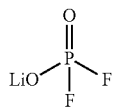

Compound C

TABLE 2

|  | Additive for non-aqueous electrolyte solution | | Initial characteristics | Storage characteristics | |
| --- | --- | --- | --- | --- | --- |
|  | Formula (I) compound (0.5 wt %) | Combined additive (0.5 wt %) | Resistance value (−20° C.) [%] | Capacity retention [%] | Resistance value (−20° C.) [%] |
| Example 7 | Exemplary compound 23 | Compound A | 89 | 108 | 67 |
| Example 8 | Exemplary compound 23 | Compound B | 70 | 104 | 71 |
| Example 9 | Exemplary compound 23 | Compound C | 63 | 108 | 59 |
| Example 10 | Exemplary compound 23 | Compound D | 95 | 106 | 71 |
| Example 11 | Exemplary compound 23 | Compound E | 71 | 102 | 65 |
| Example 12 | Exemplary compound 23 | Compound F | 90 | 103 | 58 |
| Example 13 | Exemplary compound 23 | Compound G | 65 | 107 | 55 |
| Example 14 | Exemplary compound 10 | Compound A | 89 | 104 | 77 |
| Example 15 | Exemplary compound 10 | Compound B | 87 | 98 | 86 |
| Example 16 | Exemplary compound 10 | Compound C | 93 | 102 | 70 |
| Example 17 | Exemplary compound 10 | Compound D | 95 | 98 | 80 |
| Example 18 | Exemplary compound 10 | Compound E | 92 | 102 | 73 |
| Example 19 | Exemplary compound 10 | Compound F | 96 | 103 | 62 |
| Example 20 | Exemplary compound 10 | Compound G | 88 | 105 | 74 |
| Example 21 | Exemplary compound 1 | Compound G | 94 | 99 | 61 |
| Example 22 | Exemplary compound 43 | Compound G | 96 | 102 | 82 |
| Example 23 | Exemplary compound 81 | Compound G | 95 | 99 | 88 |
| Comparative Example 1 | None | None | 100 | 100 | 100 |

Compound D 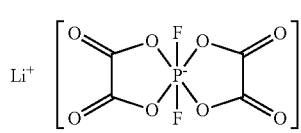

Compound E 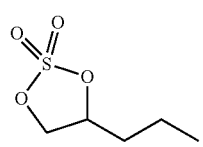

Compound F 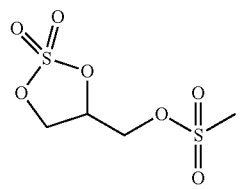

Compound G 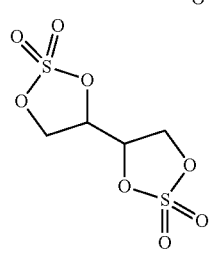

As shown in Table 2, in Examples 7 to 23 which used the combination of the compound represented by formula (1) and any one of the compounds A to G, the low temperature resistance value as one of the storage characteristics was significantly reduced with the capacity retention maintained, in comparison with Comparative Example 1 which contained no additive. In addition, in Examples 7 to 23, the low temperature resistance value as one of the initial characteristics was significantly reduced, in comparison with Comparative Example 1.

Examples 24 to 31

In each example, a coin battery was obtained in the same manner as in Examples 7 to 9, 13 to 16, and 20, except that the additive amount of the compound represented by formula (1) was increased such that the content thereof relative to the total mass of the finally obtained non-aqueous electrolyte solution would be 1.5 wt %.

The coin battery thus obtained was subjected to various measurements in the same manner as in Example 1. The evaluation results are shown in Table 3.

TABLE 3

| | Additive for non-aqueous electrolyte solution | | Initial characteristics | Storage characteristics | |
|---|---|---|---|---|---|
| | Formula (I) compound (0.5 wt %) | Combined additive (0.5 wt %) | Resistance value (−20° C.) [%] | Capacity retention [%] | Resistance value (−20° C.) [%] |
| Example 24 | Exemplary compound 23 | Compound A | 92 | 102 | 52 |
| Example 25 | Exemplary compound 23 | Compound B | 75 | 99 | 58 |
| Example 26 | Exemplary compound 23 | Compound C | 67 | 98 | 66 |
| Example 27 | Exemplary compound 23 | Compound G | 74 | 98 | 61 |
| Example 28 | Exemplary compound 10 | Compound A | 88 | 98 | 50 |
| Example 29 | Exemplary compound 10 | Compound B | 88 | 98 | 57 |
| Example 30 | Exemplary compound 10 | Compound C | 95 | 98 | 55 |
| Example 31 | Exemplary compound 10 | Compound G | 87 | 98 | 43 |
| Comparative Example 1 | None | None | 100 | 100 | 100 |

For comparison, Table 3 also shows the results of Comparative Example 1 which have been shown in Table 2.

As shown in Table 3, the same effect as in Examples 7 to 9, 13 to 16, and 20 was also confirmed in Examples 24 to 31 wherein an added amount of the compound represented by formula (1) was increased compared to in Examples 7 to 9, 13 to 16, and 20.

The entire disclosures of Japanese Patent Application No. 2011-231618 is incorporated in this specification by reference.

All publications, patent applications, and technical standards mentioned in this specification are herein incorporated by reference to the same extent as if each individual publication, patent application, or technical standard was specifically and individually indicated to be incorporated by reference.

The invention claimed is:

1. A non-aqueous electrolyte solution comprising a phosphonosulfonic acid compound represented by the following formula (I); and a lithium salt as an electrolyte:

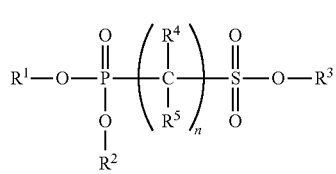

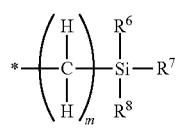

wherein, in formula (I), $R^1$, $R^2$ and $R^3$ each independently represent a hydrogen atom, an alkyl group having 1 to 6 carbon atoms, a haloalkyl group having 1 to 6 carbon atoms, a phenyl group, a benzyl group, or a group represented by the above formula (II); $R^4$ and $R^5$ each independently represent a hydrogen atom, a halogen atom, or an alkyl group having 1 to 6 carbon atoms; and n represents an integer from 1 to 6; and wherein, in formula (II), $R^6$, $R^7$ and $R^8$ each independently represent an alkyl group having 1 to 6 carbon atoms, a phenyl group, or a benzyl group; m represents an integer from 0 to 2; and * represents a position of bonding with the oxygen atom in formula (I).

2. The non-aqueous electrolyte solution according to claim 1, wherein the phosphonosulfonic acid compound represented by formula (I) is a phosphonosulfonic acid compound represented by the following formula (III):

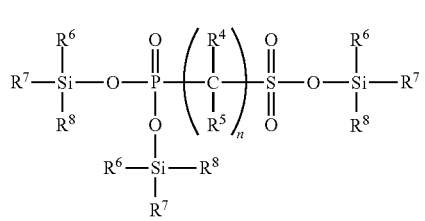

wherein, in formula (III), $R^4$ and $R^5$ each independently represent a hydrogen atom, a halogen atom, or an alkyl group having 1 to 6 carbon atoms; $R^6$, $R^7$ and $R^8$ each independently represent an alkyl group having 1 to 6 carbon atoms, a phenyl group, or a benzyl group; and n represents an integer from 1 to 6.

3. The non-aqueous electrolyte solution according to claim 1, further comprising a compound represented by the following formula (IV):

wherein, in formula (IV), $Y^1$ and $Y^2$ each independently represent a hydrogen atom, a methyl group, an ethyl group, or a propyl group.

4. The non-aqueous electrolyte solution according to claim 3, wherein the content of the compound represented by formula (IV) is from 0.001% by mass to 10% by mass relative to the total mass of the non-aqueous electrolyte solution.

5. The non-aqueous electrolyte solution according to claim 1, further comprising a compound represented by the following formula (V):

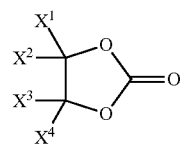

wherein, in formula (V), $X^1$, $X^2$, $X^3$ and $X^4$ each independently represent a vinyl group; an alkyl group having 1 to 3 carbon atoms, which may be substituted with a fluorine atom; a hydrogen atom; a fluorine atom; or a chlorine atom; provided that $X^1$, $X^2$, $X^3$ and $X^4$ are not all hydrogen atoms at the same time.

6. The non-aqueous electrolyte solution according to claim 5, wherein the content of the compound represented by formula (V) is from 0.001% by mass to 10% by mass relative to the total mass of the non-aqueous electrolyte solution.

7. The non-aqueous electrolyte solution according to claim 1, further comprising a compound represented by the following formula (VI):

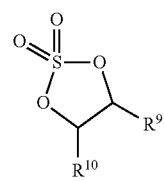

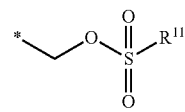

-continued (VIII)

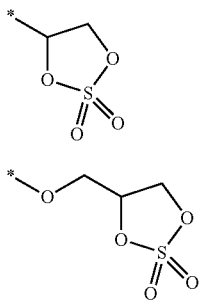

(IX)

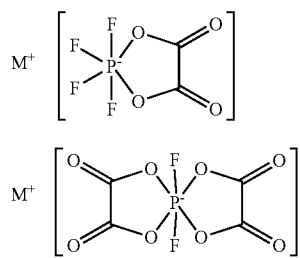

wherein, in formula (VI), $R^9$ and $R^{19}$ each independently represent a hydrogen atom, an alkyl group having 1 to 6 carbon atoms, a group represented by the above formula (VII), or a group represented by the above formula (VIII);

wherein, in formula (VII), $R^{11}$ represents a halogen atom, an alkyl group having 1 to 6 carbon atoms, a haloalkyl group having 1 to 6 carbon atoms, an alkoxy group having 1 to 6 carbon atoms, or a group represented by the above formula (IX); and wherein, in formulae (VII), (VIII), and (IX), * represents a position of bonding.

8. The non-aqueous electrolyte solution according to claim 7, wherein the content of the compound represented by formula (VI) is from 0.001% by mass to 10% by mass relative to the total mass of the non-aqueous electrolyte solution.

9. The non-aqueous electrolyte solution according to claim 1, further comprising at least one compound selected from the group consisting of lithium difluorophosphate (LiOP(O)F$_2$), a compound represented by the following formula (X), a compound represented by the following formula (XI), and a compound represented by the following formula (XII):

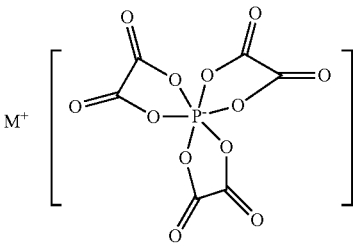

(XII)

wherein, in formulae (X), (XI), and (XII), M represents an alkali metal.

10. The non-aqueous electrolyte solution according to claim 9, wherein a total content of lithium difluorophosphate (LiOP(O)F$_2$), the compound represented by formula (X), the compound represented by formula (XI), and the compound represented by formula (XII) is from 0.001% by mass to 10% by mass relative to the total mass of the non-aqueous electrolyte solution.

11. The non-aqueous electrolyte solution according to claim 1, wherein the content of the phosphonosulfonic acid compound represented by formula (I) is from 0.001% by mass to 10% by mass relative to the total mass of the non-aqueous electrolyte solution.

12. The non-aqueous electrolyte solution according to claim 1, wherein the lithium salt as an electrolyte is at least one selected from the group consisting of LiPF$_6$, LiBF$_4$, LiClO$_4$, LiAsF$_6$, Li$_2$SiF$_6$, LiOSO$_2$C$_k$F$_{(2k+1)}$ (k is an integer from 1 to 8), LiPF$_n$[C$_k$F$_{(2k+1)}$]$_{(6-n)}$ (n is an integer from 1 to 5, k is an integer from 1 to 8), LiC(SO$_2$R$^a$)(SO$_2$R$^b$)(SO$_2$R$^c$) (wherein R$^a$, R$^b$ and R$^c$ may be identical or different, and are perfluoroalkyl groups having 1 to 8 carbon atoms), LiN(SO$_2$OR$^d$)(SO$_2$OR$^e$) (wherein R$^d$ and R$^e$ may be identical or different, and are perfluoroalkyl groups having 1 to 8 carbon atoms), and LiN(SO$_2$R$^f$)(SO$_2$R$^g$) (wherein R$^f$ and R$^g$ may be identical or different, and are perfluoroalkyl groups having 1 to 8 carbon atoms).

13. The non-aqueous electrolyte solution according to claim 1, wherein the lithium salt as an electrolyte comprises LiPF$_6$.

14. A lithium secondary battery, comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the non-aqueous electrolyte solution according to claim 1.

* * * * *